(12) United States Patent
Chang et al.

(10) Patent No.: US 11,013,779 B2
(45) Date of Patent: May 25, 2021

(54) SMALL MOLECULE THERAPEUTIC INHIBITORS AGAINST PICORNAVIRUSES, CALICIVIRUSES, AND CORONAVIRUSES

(71) Applicants: Kansas State University Research Foundation, Manhattan, KS (US); Wichita State University, Wichita, KS (US)

(72) Inventors: Kyeong-Ok Chang, Manhattan, KS (US); Yunjeong Kim, Manhattan, KS (US); William C. Groutas, Wichita, KS (US)

(73) Assignees: Kansas State University Research Foundation, Manhattan, KS (US); Wichita State University, Wichita, KS (US)

( * ) Notice: Subject to any disclaimer, the term of this patent is extended or adjusted under 35 U.S.C. 154(b) by 117 days.

(21) Appl. No.: 16/311,108

(22) PCT Filed: Jun. 16, 2017

(86) PCT No.: PCT/US2017/037920
§ 371 (c)(1),
(2) Date: Dec. 18, 2018

(87) PCT Pub. No.: WO2017/222935
PCT Pub. Date: Dec. 28, 2017

(65) Prior Publication Data
US 2020/0230198 A1 Jul. 23, 2020

Related U.S. Application Data

(60) Provisional application No. 62/352,294, filed on Jun. 20, 2016, provisional application No. 62/376,097, filed on Aug. 17, 2016.

(51) Int. Cl.
*A61K 38/05* (2006.01)
*A61P 31/14* (2006.01)

(52) U.S. Cl.
CPC .............. *A61K 38/05* (2013.01); *A61P 31/14* (2018.01)

(58) Field of Classification Search
CPC .... A61K 38/05; A61K 38/03; A61K 31/4015; A61K 31/454; A61K 45/06; A61P 31/14; C07K 5/06043; Y02A 50/30
See application file for complete search history.

(56) References Cited

U.S. PATENT DOCUMENTS

| 2005/0090432 | A1 | 4/2005 | McPhee et al. |
| 2005/0119169 | A1 | 6/2005 | Deslongchamps et al. |
| 2009/0130059 | A1 | 5/2009 | Sun et al. |
| 2014/0243341 | A1* | 8/2014 | Chang ................ A61K 31/5377 514/237.2 |
| 2015/0133368 | A1 | 5/2015 | Chang et al. |

OTHER PUBLICATIONS

Yu, Xufen "Macrocycfic Drugs and Synthetic Methodologies toward Macrocycles," MOlecules, May 24, 2013, pp. 6230-6268, vol. 18.
Galasiti Kankanamalage, Anushka C. "Structure-Guided Design and Optimization of Dipeptidyl Inhibitors of Norovirus 3CL Protease. Structure—Activity Relationship and Biochemical, x-ray Crystallographic, Cell-Based and in Vivo Studies," Journal of Medicinal Chemistry, Mar. 12, 2015, pp. 3144-3155, vol. 58.
Mandadapu, Sivakoteswara Rao "Inhibition of norovirus 3CL protease by bisulfite adducts of transition state inhibitors," Biorganic & Medicinal Chemistry Letters, 2013, pp. 62-65, vol. 23.
The International Search Report and Written Opinion dated Sep. 6, 2017, in PCT/US2017/037920 filed Jun. 16, 2017.

* cited by examiner

*Primary Examiner* — Sudhakar Katakam
(74) *Attorney, Agent, or Firm* — Hovey Williams LLP

(57) ABSTRACT

Antiviral protease inhibitors are disclosed, along with related antiviral dipeptidyl compounds, macrocyclic derivatives thereof and methods of using the same to treat or prevent viral infection and disease from coronaviruses, caliciviruses, and picornaviruses.

7 Claims, 12 Drawing Sheets

Specification includes a Sequence Listing.

Synthesis of GC813 and prodrug varients (I-III)

|  | MERS-CoV | | FIPV | | MHV | CC50 (µM) |
| --- | --- | --- | --- | --- | --- | --- |
|  | IC50 | EC50 | IC50 | EC50 | EC50 |  |
| GC376 | 1.6 | 0.9 | 0.7 | 0.05 | 1.1 | > 150 |
| GC813 | 0.7 | 0.5 | 1.8 | 0.6 | 0.6 | > 150 |
| GC817 | 1.8 | 1.1 | ND | 0.4 | 0.8 | > 150 |
| GC819 | 2.1 | 0.3 | ND | 0.5 | 1.2 | > 150 |
| GC821 | 3.1 | 0.7 | ND | 1.1 | 0.6 | > 150 |
| GC833 | 0.6 | 0.3 | ND | 0.4 | 0.5 | > 150 |

$^a$ TEA/ acetonitrile/ reflux/ 2h; $^b$1M LiOH(aq)/ THF/ RT/ 3h; $^c$EDCI/ HOBt/ DIEA/ DMF; $^d$2M LiBH$_4$/ THF/ CH$_3$OH; $^e$Dess-Martin periodinane/ DCM; $^f$C$_2$H$_5$OH/ EtOAc/ NaHSO$_3$

|  | R1 | R2 | MERS-CoV IC$_{50}$ | MERS-CoV EC$_{50}$ | FIPV IC$_{50}$ | FIPV EC$_{50}$ | MHV EC$_{50}$ | CC$_{50}$ (µM) |
|---|---|---|---|---|---|---|---|---|
| GC376 | - | - | 1.6 | 0.9 | 0.7 | 0.02 | 1.1 | > 150 |
| GC813 | - | - | 0.7 | 0.5 | 1.8 | 0.6 | 0.6 | > 150 |
| GC867 | H | CH$_3$SO$_2$ | 0.5 | ND | 3.5 | 2.0 | 0.5 | > 150 |
| GC868 | H | Boc | 0.3 | 0.2 | 2.4 | 1.5 | 0.3 | > 150 |
| GC861 | C$_6$H$_5$CH$_2$ | Boc | 0.6 | 0.8 | 1.5 | 0.8 | 0.6 | > 150 |

Design of R₄ of GC868

$^a$HCl/THF; $^b$RSO₂Cl/DIEA/DCM or RO(CO)Cl/DIEA/DCM; $^c$LiBH₄/ THF/ CH₃OH; $^d$Dess-Martin periodinane/DCM; $^e$NaHSO₃/aq EtOAc/EtOH Synthesis of alpha-ketoamides using the Passerini reaction/design of R'

$^a$(L) N-Boc-Leu-OH/RNC or RONC or RCH(COOCH₃)NC/DCM/RT;
$^b$TFA/DCM

Design of R₃ of GC868

Z= CH(OH)SO₃Na (Ia); (CO)CONHR (Ib);
(CO)CONHOR (Ic);
(CO)CONHCHRCOOCH₃ (Id)

ᵃR₃MgBr/THF; ᵇ4M HCl/dioxane; ᶜR₄SO₂Cl or R₄O(CO)Cl/DIEA/DCM; ᵈLiBH₄/THF; ᵉDess-Martin; ᶠNaHSO₃/aq EtOAc or RNC or RCH(COOCH₃)NC followed by Dess-Martin ᵃ ⌬_MgCl; ᵇR₂CH(N=C=O)COOCH₃; ᶜLiOH/aq/THF; ᵈEDCI/HOBt/DIEA/DMF then (HCl)NH₂CH(COOCH₃)(CH₂)₂(C=O)NH(CH₂)ₘ⌬ ; ᵉGrubb's catalyst; ᶠH2/Pd-C; ᵍTFA/DCM;

ʰRSO₂Cl or RO(C=O)Cl; ⁱLiBH₄/THF; ʲDess-Martin periodinane; ᵏNaHSO₃/aq EtOAC,EtOH/H₂O

SMALL MOLECULE THERAPEUTIC INHIBITORS AGAINST PICORNAVIRUSES, CALICIVIRUSES, AND CORONAVIRUSES

CROSS-REFERENCE TO RELATED APPLICATIONS

The present application is the U.S. National Stage of International Patent Application No. PCT/US2017/037920, filed Jun. 16, 2017, which claims the priority benefit of U.S. Provisional Patent Application Ser. No. 62/352,294, filed Jun. 20, 2016, and Ser. No. 62/376,097, filed Aug. 17, 2016, both entitled SMALL MOLECULE THERAPEUTIC INHIBITORS AGAINST CORONAVIRUSES INCLUDING MERS-CoV, and incorporated by reference in their entireties herein.

STATEMENT REGARDING FEDERALLY-FUNDED RESEARCH

This invention was made with U.S. Government support under grant number R01 AI1109039 awarded by the National Institute of Health. The U.S. Government has certain rights in the invention.

SEQUENCE LISTING

The nucleic and amino acid sequences listed in the accompanying Sequence Listing are presented in accordance with 37 C.F.R. 1.822. Only one strand of each nucleic acid sequence is shown, but the complementary strand is understood as included by any reference to the displayed strand. The Sequence Listing is submitted as an ASCII computer readable text file, created on Jun. 15, 2017, 1 KB, which is incorporated by reference herein.

BACKGROUND OF THE INVENTION

Field of the Invention

The present invention relates to small molecule antiviral compounds targeting the 3C or 3C-like proteases of the picornavirus-like supercluster, and specific coronaviruses, caliciviruses, and picornaviruses.

Description of Related Art

Coronaviruses infect humans and animals causing a broad spectrum of diseases. Many viruses, including coronaviruses, encode polyproteins with proteases which catalyze their subsequent cleavage to the mature functional proteins and are essential for viral replication. In 2003, a severe acute respiratory syndrome coronavirus (SARS-CoV) emerged as the cause of outbreaks of a life threatening form of pneumonia. More recently, a novel highly-pathogenic coronavirus, Middle East respiratory syndrome (MERS-CoV), emerged suddenly in Saudi Arabia as the cause of severe respiratory illness in humans. MERS-CoV expresses two polyproteins which undergo proteolytic processing by two virus-encoded proteases, a 3C-like protease (3CLpro) and a papain-like protease (PLpro), to generate functionally active proteins. 3CLpro processes the majority of the cleavage sites on the polyproteins, making it an attractive therapeutic target.

Since its occurrence in 2012, MERS-CoV infection has largely been confined to the Middle East. However, the unexpected outbreaks in South Korea in 2015 raises concerns that MERS-CoV may become a threat to global public health and MERS-CoV is designated as a Category C Priority Pathogens by the National Institute of Allergy and Infectious Diseases (NIAID). Despite the high mortality rate of ~40% and the significant potential for a public health emergency, there are no approved therapies or vaccines for the prevention or treatment of MERS.

Consequently, there is an urgent and unmet need for the development of antiviral therapeutics for the treatment and prevention of MERS infection. There is also a need for antiviral therapies for treating and preventing other types of coronaviruses, as well as caliciviruses and picornaviruses.

SUMMARY OF THE INVENTION

This work involves small molecule peptidyl transition state inhibitors that are active against 3CLpro of coronaviruses, and other members of the picornavirus-like supercluster. These compounds are highly effective against MERS-CoV 3CLpro in enzyme or cell-based assays with $IC_{50}$ or $EC_{50}$ values in submicromolar ranges. Feline infectious peritonitis coronavirus (FIPV) was used as a model for preliminary in vivo testing, because its pathogenesis is primarily immunemediated (similar to SARS- and MERS-CoV). One of the compounds has been demonstrated to reverse the progression of fatal FIP. The results suggested that an effective viral protease inhibitor alone could reverse the immune-mediated pathogenesis in affected hosts. The compounds disclosed in this form are new compounds more specific to MERS-CoV. These compounds are also effective against other coronaviruses, and other members of the picornavirus-like supercluster, including caliciviruses and picornaviruses, and have potential to develop further preclinical/clinical test compounds.

In one aspect, an antiviral compound comprising formula (I) or formula (II), or a pharmaceutically-acceptable salt thereof is provided:

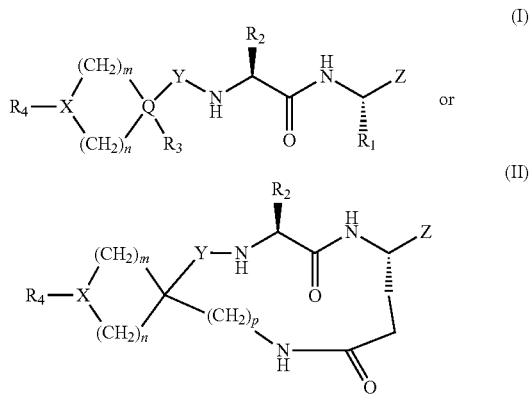

m and n are each individually 1, 2, or 3; p is 4, 5, 6, 7, 8, 9, or 10; each X is CH or N; each Y is selected from the group consisting of —O(C=O)—, —$SO_2$—, and —NH(C=O)—; each Z is selected from the group consisting of —CHO, —CH(OH)$SO_3$Na, —CH(O(C=O)R)$SO_3$Na, —CH(O(C=O)OR)$SO_3$Na, —CH(O(C=O)NHR)$SO_3$Na, —(C=O)(C=O)NHR, —(C=O)(P=O)(OR)$_2$, —CN, —(C=O)COOR, and substituted or unsubstituted heterocycles, where each R is selected from the group consisting of alkyls, haloalkyls, phenyls, and arylalkyls; each Q is CH, CR, or N; each $R_1$ is Gln or a Gln surrogate side chain; each $R_2$ is selected from the group consisting of branched or unbranched alkyls and natural or unnatural amino acids; each $R_3$ is selected from the group consisting of —H, branched or unbranched alkyls, substituted or unsubstituted aryls, and arylalkyls; and each $R_4$ is selected from the group consisting of branched or unbranched alkyls, substituted or unsubstituted aryls, arylalkyls, —$SO_2R$, —$SO_2NH_2$, —$SO_2NRR$, and —COOR, where each R is selected from the group consisting of alkyls, haloalkyls, phenyls, and arylalkyls.

Novel antiviral dipeptidyl compounds are also disclosed. Such compounds comprise formula (III):

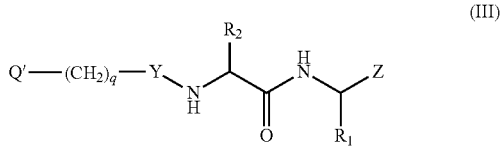

(III)

where Z is selected from the group consisting of —CHO, —CH(OH)SO$_3$Na, —CH(O(C=O)R)SO$_3$Na, —CH(O(C=O)OR)SO$_3$Na, —CH(O(C=O)NHR)SO$_3$Na, —(C=O)(C=O)NHR, —(C=O)(P=O)(OR)$_2$, —CN, —(C=O)COOR, and substituted or unsubstituted heterocycles, where each R is selected from the group consisting of alkyls, haloalkyls, phenyls, and arylalkyls; $R_1$ is selected from the group consisting of is Gln or a Gln surrogate; $R_2$ is selected from the group consisting of branched or unbranched alkyls, and natural or unnatural amino acids; Y is selected from the group consisting of —O(C=O)—, —$SO_2$—, —NH(C=O)—; q is 1, 2, 3, 4, 5, 6, 7, 8, 9, 10, 11, or 12; and Q' is a —H, substituted or unsubstituted phenyl, halogenated phenyl, or combination thereof. Specific examples of such compounds include:

GC813

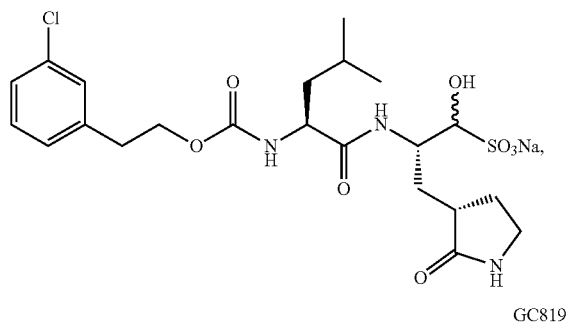

GC819

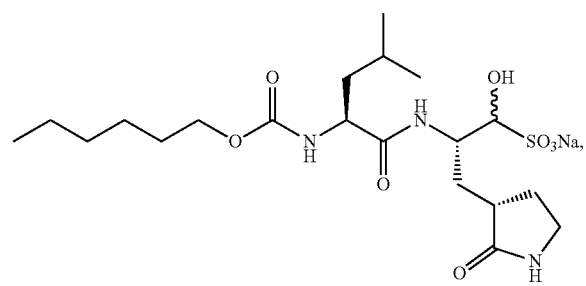

GC821

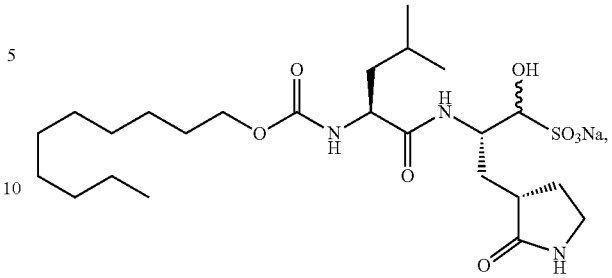

or pharmaceutically-acceptable salts thereof.

A method of treating or preventing viral infection in a subject from one or more viruses selected from the group consisting of caliciviruses, picornaviruses, and/or coronaviruses is also provided. The method comprises administering to said subject a therapeutically-effective amount of a first antiviral compound according to the various embodiments described herein.

A broad spectrum antiviral composition is also disclosed. The composition comprises a first antiviral compound according to the various embodiments described herein dispersed in a pharmaceutically-acceptable carrier.

A kit is also provided herein. The kit comprises: an antiviral compound according to the various embodiments described herein; and instructions for administering the compound to a subject in need thereof.

A method of preventing or inhibiting replication of a virus in a cell is also disclosed. The method comprises contacting the cell with a compound according to the various embodiments described herein, wherein the virus is selected from the group consisting of caliciviruses, picornaviruses, coronaviruses, and combinations thereof.

The invention is also concerned with the use of a compound according to the various embodiments described herein to prepare a therapeutic or prophylactic medicament for the treatment or prevention of a viral infection from caliciviruses, picornaviruses, and/or coronaviruses in a subject.

DETAILED DESCRIPTION

Figure 1:
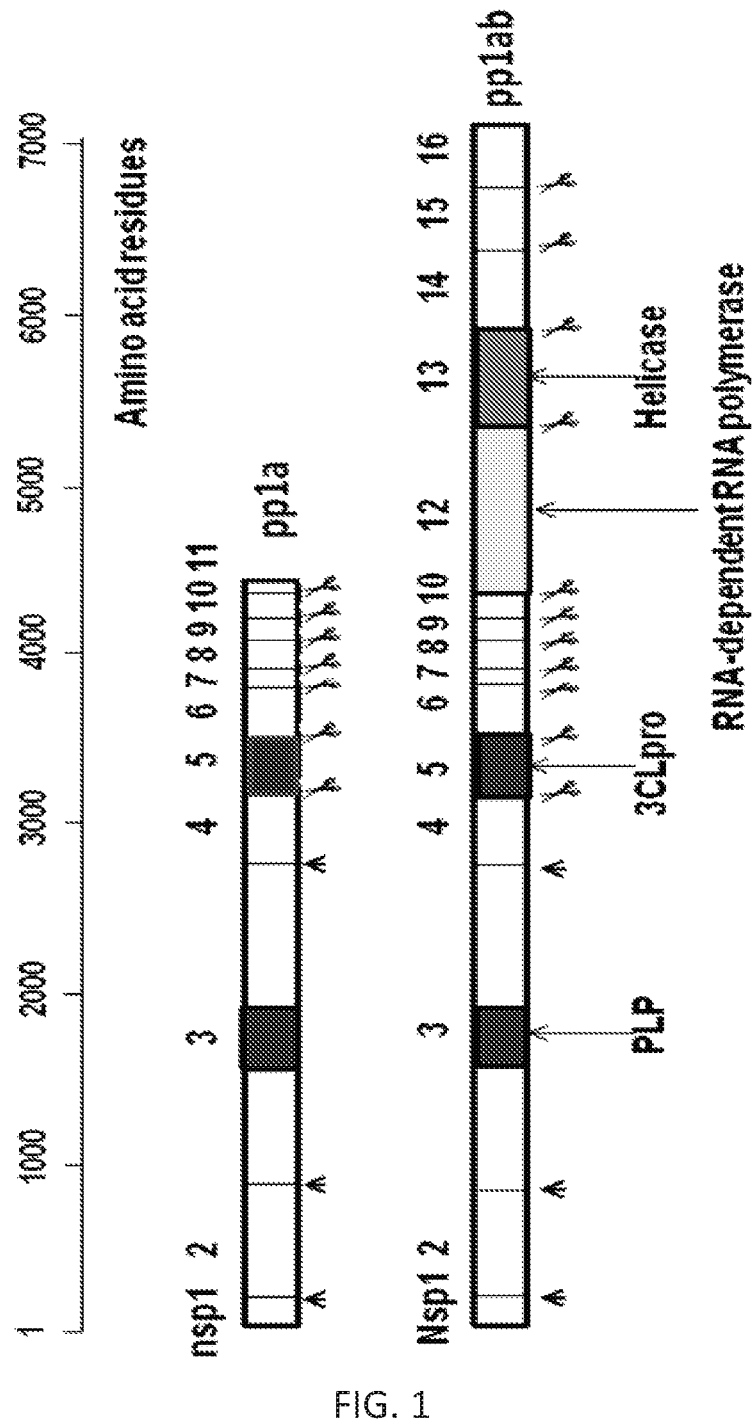
FIG. 1 is an illustration of an overview of the organization and proteolytic processing of MERS-CoV polyproteins, pp1a and pp1b. Scissor images indicate cleavages by 3CLpro, and black arrowheads by PLpro.

Among positive sense RNA viruses, genetic analysis has demonstrated that certain viruses can be classified as members of the picornavirus-like "supercluster," which includes picornaviruses, caliciviruses, and coronaviruses. A common feature of these viruses is that they possess a viral 3C or 3CL protease which is responsible for most cleavages of the corresponding viral polyprotein. These 3C and 3CL proteases share some common characteristics, including a typical chymotrypsin-like fold and a catalytic triad (or dyad) with Cys-His-Glu (or Asp) on the protease, and a preference for a Glu or Gln residue at the P1 position on the substrate. High resolution 3D structures of these proteases have confirmed the conservation of active sites with the catalytic triad or dyad and substrate binding pockets. Viruses in the picornavirus-like supercluster include important human and animal pathogens. For example, caliciviruses include noroviruses (Norwalk virus [NV]), feline calicivirus, MD145, murine norovirus [MNV], vesicular exanthema of swine virus, and rabbit hemorrhagic disease virus. Picornaviruses include enteroviruses (such as enterovirus 71), poliovirus, coxsackievirus, foot-and-mouth disease virus (FMDV), hepatitis A virus (HAV), porcine teschovirus, and rhinovirus (cause of common cold). Coronaviruses include human coronavirus (cause of common cold such as 229E strain), transmissible gastroenteritis virus (TGEV), murine hepatitis virus (MHV), bovine coronavirus (BCV), feline infectious peritonitis virus (FIPV), severe acute respiratory syndrome coronavirus (SARS-Co), and Middle East respiratory syndrome coronavirus (MERS-CoV).

A series of novel protease inhibitors have been synthesized and demonstrated to possess efficacy against viruses that belong to the picornavirus-like supercluster in enzyme and/or cell based assays, as well as in in vivo animal models. These antiviral compounds are inhibitors of virally-encoded 3C-like protease (3CLpro) with broad activity specifically against MERS-CoV, as well as other human and animal coronaviruses. The compounds include dipeptidyl viral protease inhibitors, including piperidine-based compounds and macrocyclic derivatives thereof. Members of this series of compounds are highly effective as antiviral therapeutics targeting a specific virus or, more importantly, they are broad-spectrum antivirals targeting multiple viruses. The wide applicability of the latter constitutes a significant advance in antiviral research and public health.

Embodiments described herein include antiviral compounds having broad-spectrum (multivalent) activity against viruses that belong to the picornavirus-like supercluster, including caliciviruses, picornaviruses and coronaviruses. The compounds are small-molecule based antivirals. These compounds have broad-spectrum therapeutic value against multiple viruses of the picornavirus-like supercluster, which includes important classical and emerging animal and human pathogens. The compounds effectively target and inhibit viral 3C or 3CL protease activity across multiple virus species, strains, and subtypes, thereby preventing formation of the mature virus and inhibiting virus replication in the host cell. In some embodiments, the compounds are prodrugs that are converted into active compounds that target and inhibit viral 3C or 3CL protease activity. The compounds have a therapeutic index (ratio of lethal or toxic dose to therapeutic dose) of greater than about 500:1, indicating the relative safety of such compounds for use in human and veterinary applications.

In some embodiments, antiviral compounds comprising (consisting essentially or even consisting of) formula (I), or the pharmaceutically-acceptable salt thereof, are provided:

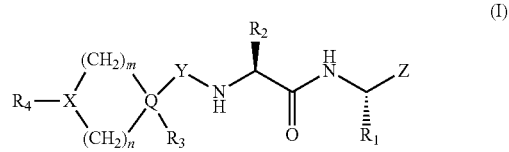

(I)

where, Z is selected from the group consisting of —CHO, —CH(OH)SO$_3$Na, —CH(O(C=O)R)SO$_3$Na, —CH(O(C=O)OR)SO$_3$Na, —CH(O(C=O)NHR)SO$_3$Na, —(C=O)(C=O)NHR, —(C=O)(P=O)(OR)$_2$, —CN, —(C=O)COOR, and substituted or unsubstituted heterocycles, where each R is selected from the group consisting of alkyls (preferably $C_1$-$C_6$ alkyls), haloalkyls, phenyls, and arylalkyls (preferably $C_4$-$C_{12}$ arylalkyls); $R_1$ is Gln or a Gln surrogate (i.e., any side chain capable of functioning like Gln by engaging in critical hydrogen bonding interactions with Thr134 and His157, such as —CH$_2$W where W is 1-pyrrolidinyl, 3-pyrrolidinyl, —CH$_2$CON(CH$_3$)$_2$, or —CH$_2$NHCOR$_5$, where R$_5$ is alkyl, phenyl or arylakyl); R$_2$ is selected from the group consisting of branched or unbranched $C_1$-$C_6$ alkyls, and natural or unnatural amino acids; R$_3$ is selected from the group consisting of —H, branched or unbranched alkyls (preferably $C_1$-$C_6$ alkyls), substituted or unsubstituted $C_3$-$C_6$ aryls (e.g., substituted or unsubstituted phenyl), and arylalkyls (preferably $C_4$-$C_{12}$ arylalkyls); Y is selected from the group consisting of —O(C=O)—, —SO$_2$—, and —NH(C=O)—; m and n are each individually 1, 2, or 3; X is CH or N; Q is CH, CR, or N; and R$_4$ is selected from the group consisting of branched or unbranched alkyls (preferably $C_1$-$C_6$ alkyls), substituted or unsubstituted aryls (preferably $C_3$-$C_6$ aryls, e.g., substituted or unsubstituted phenyl), arylalkyls (preferably $C_4$-$C_{12}$ arylalkyls), —SO$_2$R, —SO$_2$NH$_2$, —SO$_2$NRR, and —COOR, where each R is selected from the group consisting of alkyls (preferably $C_1$-$C_6$ alkyls), haloalkyls, phenyls, and arylalkyls (preferably $C_4$-$C_{12}$ arylalkyls). The term "pharmaceutically-acceptable salt" refers to an acid or base salt of a compound of the invention, which salt possesses the desired antiviral activity and is neither biologically nor otherwise undesirable.

In some embodiments, the compounds are piperidine-based or cyclohexane-based derivatives selected from the group consisting of:

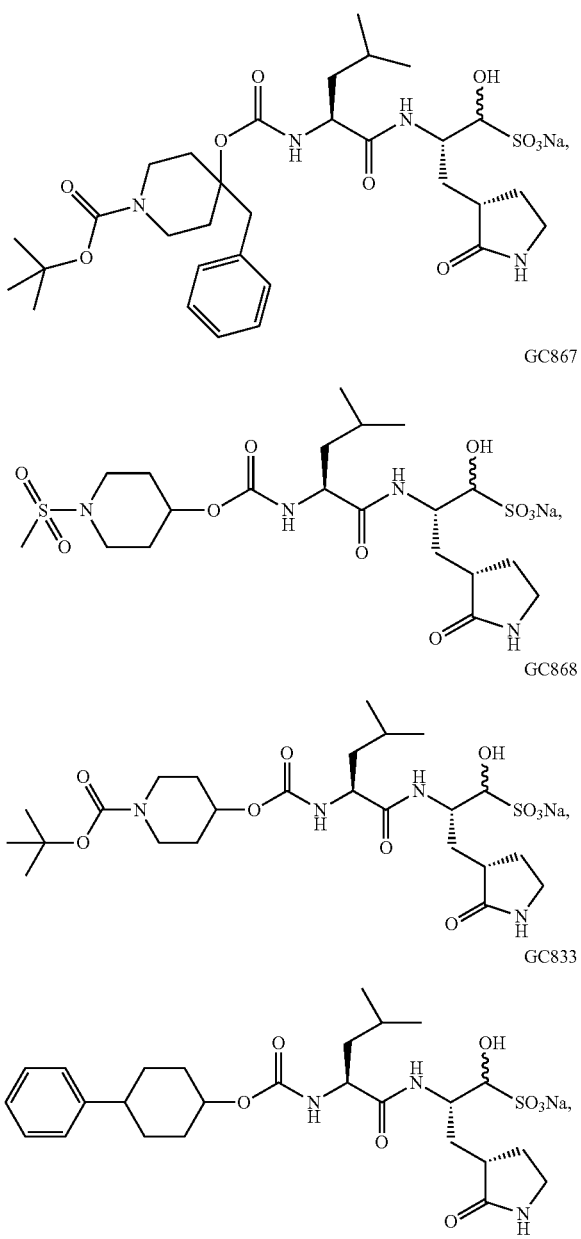

or a pharmaceutically-acceptable salt thereof.

In some embodiments, macrocyclic antiviral compounds comprising (consisting essentially or even consisting of) formula (II), or the pharmaceutically-acceptable salt thereof, are provided:

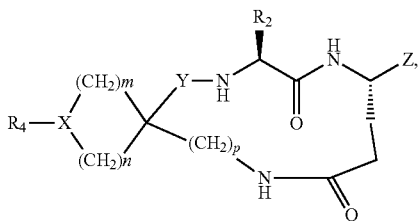

where Z is selected from the group consisting of —CHO, —CH(OH)SO$_3$Na, —CH(O(C=O)R)SO$_3$Na, —CH(O(C=O)OR)SO$_3$Na, —CH(O(C=O)NHR)SO$_3$Na, —(C=O)(C=O)NHR, —(C=O)(P=O)(OR)$_2$, —CN, —(C=O)COOR, and substituted or unsubstituted heterocycles, where each R is selected from the group consisting of alkyls (preferably $C_1$-$C_6$ alkyls), haloalkyls, phenyls, and arylalkyls (preferably $C_4$-$C_{12}$ arylalkyls); $R_2$ is selected from the group consisting of branched or unbranched alkyls (preferably $C_1$-$C_6$ alkyls), and natural or unnatural amino acids; Y is selected from the group consisting of —O(C=O)— and —SO$_2$—; m and n are each individually 1 or 2; p is 4, 5, 6, 7, 8, 9, or 10; X is CH or N; and $R_4$ is selected from the group consisting of branched or unbranched alkyls (preferably $C_1$-$C_6$ alkyls), substituted or unsubstituted aryls (preferably $C_3$-$C_6$ aryls, e.g., substituted or unsubstituted phenyl), arylalkyls (preferably $C_4$-$C_{12}$ arylalkyls), —SO$_2$R, —SO$_2$NH$_2$, —SO$_2$NRR, and —COOR, where each R is selected from the group consisting of alkyls (preferably $C_1$-$C_6$ alkyls), haloalkyls, phenyls, and arylalkyls (preferably $C_4$-$C_{12}$ arylalkyls). Macrocyclic antiviral compounds of structure (II) constitute the first class of spiro macrocyclic compounds that potentially offer advantages in terms of binding. Specifically, because the piperidine and macrocyclic rings are oriented perpendicular to one another in the compound, the piperidine ring is envisaged as inserting itself into the hydrophobic S4 pocket of the protease, augmenting favorable binding interactions.

An exemplary piperidine-based macrocyclic derivative includes:

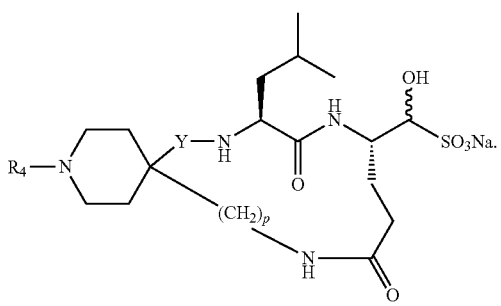

In some embodiments, the compounds are dipeptidyl compounds comprising (consisting essentially or consisting of) formula (III):

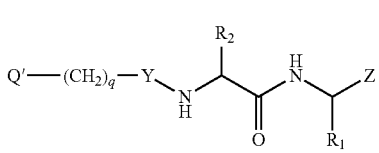

where Z is selected from the group consisting of —CHO, —CH(OH)SO$_3$Na, —CH(O(C=O)R)SO$_3$Na, —CH(O(C=O)OR)SO$_3$Na, —CH(O(C=O)NHR)SO$_3$Na, —(C=O)(C=O)NHR, —(C=O)(P=O)(OR)$_2$, —CN, —(C=O)COOR, and substituted or unsubstituted heterocycles, where each R is selected from the group consisting of alkyls (preferably C$_1$-C$_6$ alkyls), haloalkyls, phenyls, and arylalkyls (preferably C$_4$-C$_{12}$ arylalkyls); R$_1$ is selected from the group consisting of is Gln or a Gln surrogate (i.e., any side chain capable of functioning like Gln by engaging in critical hydrogen bonding interactions with Thr134 and His157, such as —CH$_2$W where W is 1-pyrrolidinyl, 3-pyrrolidinyl, CH$_2$CON(CH$_3$)$_2$, or CH$_2$NHCOR$_5$, where R$_5$ is alkyl, phenyl or arylalkyl); R$_2$ is selected from the group consisting of branched or unbranched alkyls (preferably C$_1$-C$_6$ alkyls), and natural or unnatural amino acids; Y is selected from the group consisting of —O(C=O)—, —SO$_2$—, —NH(C=O)—; q is 1, 2, 3, 4, 5, 6, 7, 8, 9, 10, 11, or 12; and Q' is a —H, substituted or unsubstituted phenyl, halogenated phenyl, or combination thereof.

In some embodiments, the compounds are dipeptidyl compounds selected from the group consisting of:

GC813

GC817

GC819

GC821 and pharmaceutically acceptable salts thereof. Combinations of one or more of the foregoing compounds can also be used in the invention. Embodiments of the invention are also concerned with compounds for treating new diseases, such as MERS-CoV. Such compounds have increased specificity for MERS-CoV. Exemplary compounds include compounds comprising formula (I), compounds comprising formula (II), and dipeptidyl antiviral compounds described above.

Prophylactic and/or therapeutic compositions with specific or broad-spectrum antiviral activities are also disclosed. The compositions comprise an antiviral compound described herein dispersed in a pharmaceutically-acceptable carrier. The term carrier is used herein to refer to diluents, excipients, vehicles, and the like, in which the antiviral may be dispersed for administration. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the compound or other agents and to minimize any adverse side effects in the subject, as would be well known to one of skill in the art. Pharmaceutically-acceptable ingredients include those acceptable for veterinary use as well as human pharmaceutical use, and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), various oil-in-water or water-in-oil emulsions, as well as dimethyl sulfoxide (DMSO), or other acceptable vehicles, and the like.

The composition can comprise a therapeutically effective amount of the compound dispersed in the carrier. As used herein, a "therapeutically effective" amount refers to the amount that will elicit the biological or medical response of a tissue, system, or subject that is being sought by a researcher or clinician, and in particular elicit some desired therapeutic or prophylactic effect as against the viral infection by preventing and/or inhibiting 3C or 3CL protease activity and/or viral replication. One of skill in the art recognizes that an amount may be considered therapeutically "effective" even if the condition is not totally eradicated or prevented, but it or its symptoms and/or effects are improved or alleviated partially in the subject. In some embodiments, the composition will comprise from about 5% to about 95% by weight of an antiviral compound described herein, and preferably from about 30% to about 90% by weight of the antiviral compound, based upon the total weight of the composition taken as 100% by weight. In some embodiments, combinations of more than one type of the described antiviral compounds can be included in the composition, in which case the total levels of all such compounds will preferably fall within the ranges described above.

Other ingredients may be included in the composition, such as adjuvants, other active agents, preservatives, buffering agents, salts, other pharmaceutically-acceptable ingredients. The term "adjuvant" is used herein to refer to substances that have immunopotentiating effects and are added to or co-formulated in a therapeutic composition in order to enhance, elicit, and/or modulate the innate, humoral, and/or cell-mediated immune response against the active ingredients. Other active agents that could be included in the composition include other antiviral compounds (e.g., cathepsin inhibitors, polymerase inhibitors such as GS-5734, interferons) or any immunogenic active components (e.g., antigens) such as those that resemble a disease-causing microorganism or infectious agent, and/or are made from weakened or killed forms of the same, its toxins, subunits, particles, and/or one of its surface proteins, such that it provokes an immune response to that microorganism or infectious agent. In addition to live, modified, or attenuated vaccine components, active agents using synthetic peptides, carbohydrates, or antigens can also be used.

Compositions according to the embodiments disclosed herein are useful in treating and/or preventing viral infection from caliciviruses (noroviruses), picornaviruses, and/or coronaviruses in a subject. Thus, embodiments described herein have broad-spectrum therapeutic and/or prophylactic uses. The terms "therapeutic" or "treat," as used herein, refer to processes that are intended to produce a beneficial change in an existing condition (e.g., viral infection, disease, disorder) of a subject, such as by reducing the severity of the clinical symptoms and/or effects of the infection, and/or reducing the duration of the infection/symptoms/effects. The terms "prophylactic" or "prevent," as used herein, refer to processes that are intended to inhibit or ameliorate the effects of a future viral infection or disease to which a subject may be exposed (but is not currently infected with). In some cases the composition may prevent the development of observable morbidity from viral infection (i.e., near 100% prevention). In other cases, the composition may only partially prevent and/or lessen the extent of morbidity due to the viral infection (i.e., reduce the severity of the symptoms and/or effects of the infection, and/or reduce the duration of the infection/symptoms/effects). In either case, the compounds are still considered to "prevent" the target infection or disease.

In use, a therapeutically-effective amount of an antiviral compound is administered to a subject. In some embodiments, a composition comprising a therapeutically-effective amount of an antiviral compound is administered to a subject. Regardless, the compound or pharmaceutically acceptable salt thereof will preferably be administered to the subject in an amount sufficient to provide antiviral compound levels (independent of salt, if any) of from about 0.1 mg to about 1,000 mg of compound per kg of body weight of the subject, preferably from about 1 mg/kg to about 100 mg/kg of body weight of the subject, and more preferably from about 10 mg/kg to about 50 mg/kg of body weight of the subject. Thus, it will be appreciated that in the case of compound salts, for example, the formulation may be administered in amounts greater than the above ranges to provide sufficient levels of the active compound. In one or more embodiments, treatment protocols include oral or parenteral administration, including intravenous, subcutaneous and intramuscular routes, of the antiviral compound one to four times per day with a total daily dosage of from about 1 to about 200 mg/day per kg of the subject's bodyweight for up to 24 weeks.

In some embodiments, the subject is afflicted with or suffering from a condition (e.g., infection, disease, or disorder) before the compounds are administered, wherein methods described herein are useful for treating the condition and/or ameliorating the effects of the condition. In one or more embodiments, the methods are useful for reversing progression of the disease or condition. In other embodiments, the subject is free of a given condition before administering the compound, wherein the methods described herein are useful for preventing the occurrence or incidence of the condition and/or preventing the effects of the condition, as described above. As noted, the disclosed embodiments are suitable for various routes of administration, depending upon the particular carrier and other ingredients used. For example, the prophylactic and/or therapeutic compounds or compositions can be injected intramuscularly, subcutaneously, intradermally, or intravenously. They can also be administered via mucosa such as intranasally or orally. The compounds or compositions can also be administered through the skin via a transdermal patch.

In some embodiments, the compound or compositions can be provided in unit dosage form in a suitable container. The term "unit dosage form" refers to a physically discrete unit suitable as a unitary dosage for human or animal use. Each unit dosage form may contain a predetermined amount of the inventive compound (and/or other active agents) in the carrier calculated to produce a desired effect. In other embodiments, the compound can be provided separate from the carrier (e.g., in its own vial, ampule, sachet, or other suitable container) for on-site mixing before administration to a subject. A kit comprising the antiviral compound(s) is also disclosed herein. The kit further comprises instructions for administering the compound to a subject. The antiviral compound(s) can be provided as part of a dosage unit, already dispersed in a pharmaceutically-acceptable carrier, or it can be provided separately from the carrier. The kit can further comprise instructions for preparing the antiviral compounds for administration to a subject, including for example, instructions for dispersing the compounds in a suitable carrier.

It will be appreciated that therapeutic and prophylactic methods described herein are applicable to humans as well as any suitable animal, including, without limitation, dogs, cats, and other pets, as well as, rodents, primates, horses, cattle, pigs, etc. The methods can be also applied for clinical research and/or study. Additional advantages of the various embodiments of the disclosure will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described and claimed herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention. Except where noted, precursor, intermediate, and final compounds described in the synthesis reactions below are independently numbered in each Example.

INTRODUCTION

The coronavirus envelope contains three major viral proteins: the spike glycoprotein (S), small envelope protein (E), and M glycoprotein (M). Coronavirus entry is initiated by the binding of S protein to cell receptors (human CD26/dipeptidyl peptidase 4 [hDPP4] for MERS-CoV). In the endosome, the fusion peptide in the S protein induces fusion to endosomal membranes leading to viral RNA entry into the cytoplasm. RNA-dependent RNA polymerase (RdRp) is responsible for replication and transcription of the coronavirus RNA genome to produce genome-size and subgenomic RNAs. The viral RNAs produce polyproteins, pp1a and pp1b, that are subsequently cleaved by two virus proteases, a papain-like protease (PLpro) and 3CLpro (the main protease) into the mature functional proteins. The structural proteins, including S, M and E, assemble to form nucleocapsids containing the viral genome and are encased with its membrane on ER. These viral progenies are transported by the Golgi vesicles to the cell membrane and then released.

Coronavirus Genome Organization and Polyprotein Processing.

MERS coronavirus is an enveloped virus with a single-stranded, positive sense RNA genome of ~29.7 kb. The two large open reading frames (ORF1a and ORF1b) on the 5' end of the MERS-CoV genome encode nonstructural proteins, while those on the 3' end encode the spike glycoprotein (S), the small envelope protein (E), the membrane glycoprotein (M), and the nucleocapsid structural proteins and several accessory proteins. Translation of the genomic mRNA of ORF1a yields polyprotein pp1a. A second polyprotein (pp1b) is the product of a ribosomal frame shift that joins ORF1a together with ORF1b. ORF1a encodes a PLpro and a 3CLpro. Polyproteins pp1a and pp1b are processed by 3CLpro (11 cleavage sites) and PLpro (three cleavage sites), resulting in 16 mature nonstructural proteins (nsp) (FIG. 1). Both proteases are essential for viral replication, making them attractive targets for drug development.

MERS-CoV 3CLpro.

MERS-CoV 3CLpro is a chymotrypsin-like cysteine protease. It has two N-terminal domains containing two n-barrel chymotrypsin-like folds with the active site in the cleft between the domains, and a globular cluster comprising five helices. MERS-CoV 3CLpro has a catalytic Cys148-His41 dyad in the active site and displays a primary substrate specificity for a P1 Gln residue which is held tightly in the S1 pocket via an array of hydrogen bonds. The largely hydrophobic S2 subsite shows a strong preference for a P2 Leu residue, although Met and Phe are also accommodated. The P3 residue side chain is oriented toward the solvent, thus P3 can be highly diverse (Val, Thr, Lys), while the S4 pocket is shallow, preferring a small P4 side chain (Ala). Functional and structural studies have revealed the similarities between the 3CLpro of coronaviruses which may be exploited in the design of broad-spectrum inhibitors. Furthermore, the stringent requirement for a P1 Gln provides a measure of assurance that inhibitors of 3CLpro may display high selectivity since no host-cell proteases are known with this specificity. In summary, MERS-CoV 3CLpro is an attractive target for the design and development of MERS-CoV therapeutics.

Example 1

Structure-Guided Design of Dipeptidyl Inhibitor GC813 and Piperidine-Based Compounds.

Figure 2:
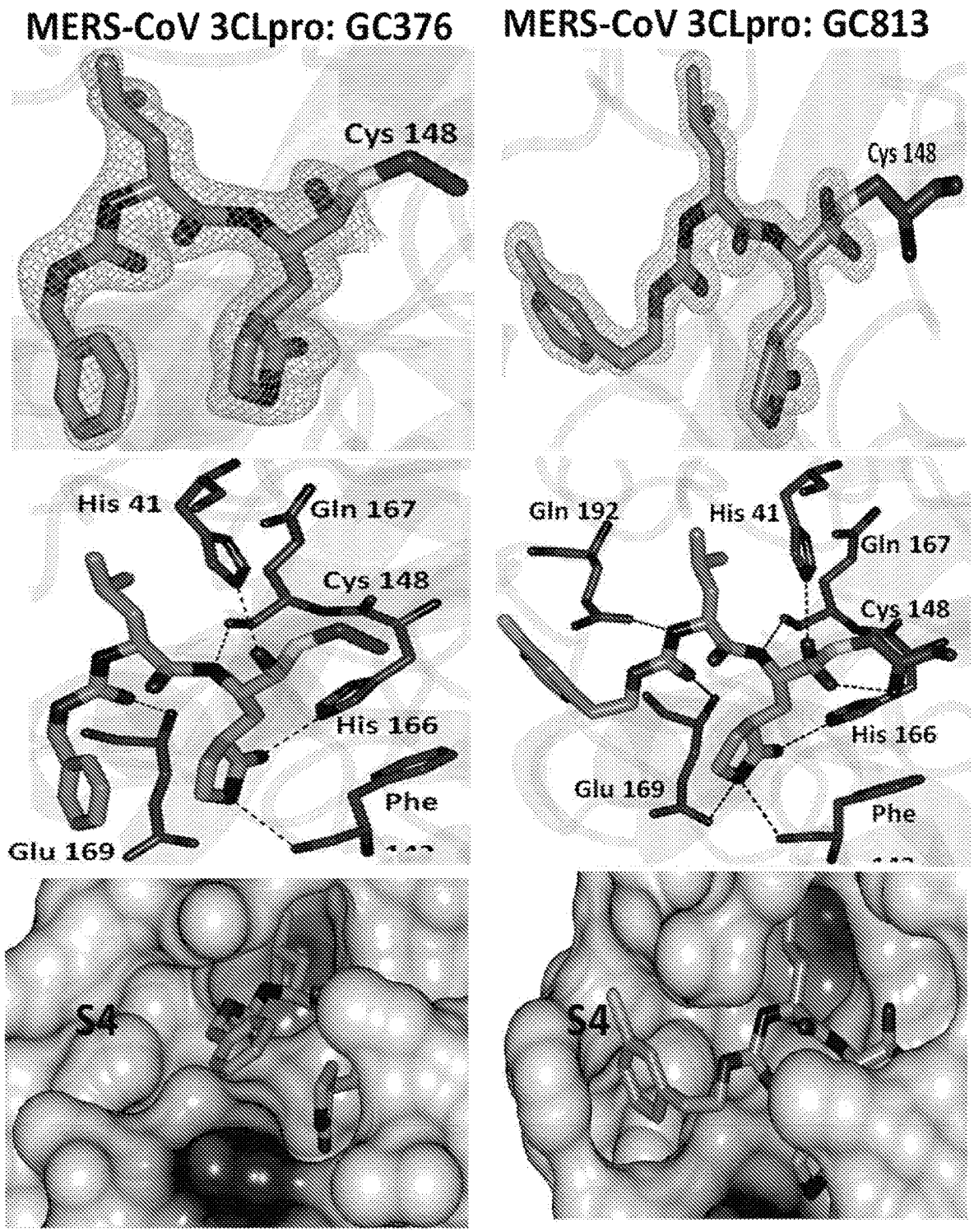
FIG. 2 is an image of X-ray co-crystallization of MERS-CoV 3CLpro: GC376 and MERS-CoV 3CLpro: GC813.

The high resolution crystal structure of MERS-CoV 3CLpro in complex with a previously-developed inhibitor compound designated as GC376 was determined. The results are shown in FIG. 2. GC 376 is described in detail in U.S. Pat. No. 9,474,759, filed Sep. 27, 2012, incorporated by reference herein.

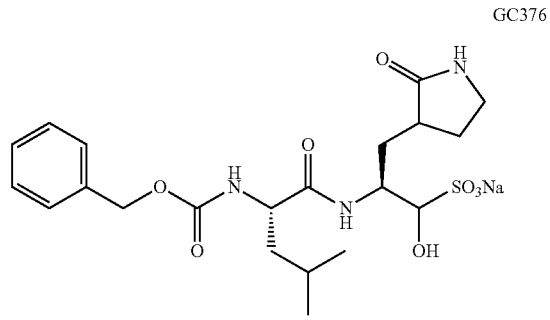

GC376

Examination of the active site of the MERS 3CLpro: GC376 complex revealed that the aldehyde bisulfite adduct had reverted to the precursor peptidyl aldehyde, which subsequently formed a tetrahedral hemithioacetal upon reaction with Cys 148. The structure reveals a network of backbone hydrogen bonds which ensure correct positioning of the inhibitor to the active site, as well as two critical hydrogen bonds with the P1 Gln surrogate side chain. The inhibitor P2 Leu side chain is snugly nestled into the hydrophobic S2 subsite of the enzyme. Importantly, the structure indicates a hydrophobic-driven interaction between the benzyl group of the inhibitor and the Gln surrogate side chain.

Based upon our extensive expertise with these viruses and the original compounds, additional structures were developed in which the "cap" is extended to permit the inhibitor compound to assume an extended conformation and orient the phenyl ring toward the hydrophobic S4 pocket of the target enzyme. Validation of these ideas was obtained by synthesizing a new antiviral compound, according to the reaction scheme illustrated in FIG. 3. This new compound is designated as GC813:

GC813

The high resolution X-ray crystal structure of the MERS-CoV 3CLpro:GC813 complex was then determined. As shown in FIG. 2, the m-Cl phenethyl side chain occupies the S4 subsite and engages in additional favorable binding interactions with the target enzyme. Additional dipeptidyl compounds were synthesized for further investigation:

GC817

GC819

GC821

Figures 3, 4:
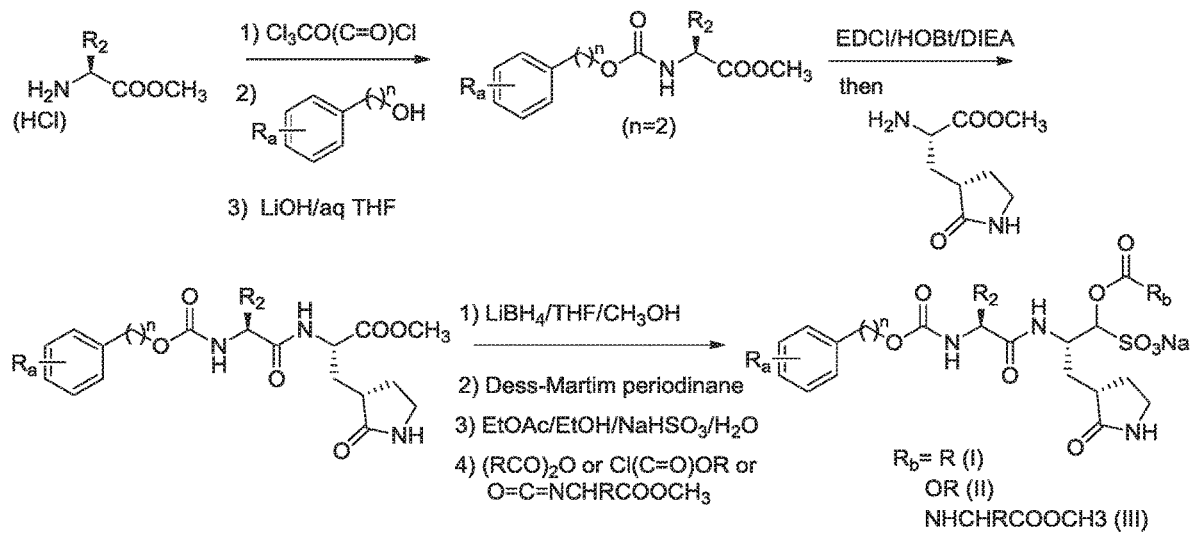
FIG. 3 is a reaction scheme depicting the synthesis of GC813 and prodrug variants.
FIG. 4 is a table of the results of enzyme and cell-based assays of effectiveness of dipeptidyl inhibitor compounds against MERS-CoV, FIPV, and MHV.

Enzyme and cell based assay to screen compounds effective against coronaviruses including feline infectious peritonitis virus (FIPV), mouse hepatitis virus (MHV) and MERS-CoV. The antiviral effects of each compound on the replication of FIPV (1146 strain), MHV (A59 strain) or MERS-CoV (EMC2013 strain) were examined in cell culture systems using CRFK, CCL-9.1 or Vero-81 cells, respectively. Briefly, confluent or semiconfluent cells were inoculated with each virus at a multiplicity of infection of 0.05 for 1 h, and the inoculum was replaced with medium containing DMSO or each compound (up to 100 uM). The virus-infected cells were further incubated for up to 96 h, and the replication of virus was measured by the 50% tissue culture infective dose (TCID50) method or plaque forming assay. The EC50s of compounds were determined using a software. The results are shown in FIG. 4, and overall, the compounds displayed broad activity against tested coronaviruses with minimal cytotoxicity.

Figure 5:
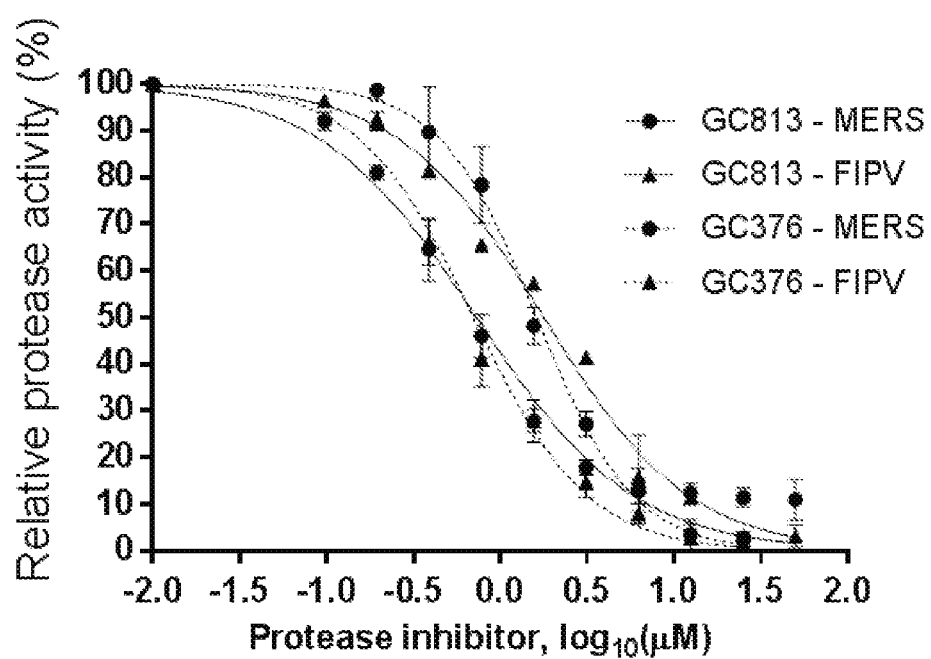
FIG. 5 is a graph of the results of FRET-based assay of dipeptidyl inhibitor compounds against MERS-CoV and FIPV.

The protease inhibition potential of the dipeptidyl compounds was also assessed using a fluorescence resonance energy transfer (FRET) protease assay. In this assay system, substrates have a fluorescence donor and a quencher on each end, and the donor fluorescence signal in the uncleaved substrate is inhibited by the interaction of the fluorescence donor and quencher. Once substrates are cleaved by a protease, the donor fluorescence is no longer quenched, yielding an increase in fluorescence intensity. Addition of protease inhibitors to the assay inhibits the cleavage of the substrates, which leads to reduced fluorescence intensity, enabling screening of potential protease inhibitors. For the enzyme assay, the codon-optimized, full-length 3CLpro from FIPV or MERS-CoV were generated and their enzymatic activity was characterized using a FRET substrate, Dabcyl-KTSAVLQ/SGFRKME-Edans (SEQ ID NO:1), derived from the cleavage sites on the coronavirus polyproteins. To examine the effects of compounds against the 3CLpro, each protease was mixed with serial dilutions of each compound, followed by the addition of assay buffer containing the substrate. Fluorescence readings were obtained, and Relative fluorescence units (RFU) were determined by subtracting background values (substrate-containing well without protease). The IC50 of each compound was determined using a software. The results are shown in FIG. 4 and FIG. 5.

Example 2

As shown in FIG. 2, the high resolution X-ray crystal structure of MERS-CoV 3CLpro in complex with dipeptidyl transition state inhibitor GC813 shows that in addition to an array of H-bonds with Gln192, Glu169, and Gln167, and the backbone of the inhibitor which serve to correctly position the inhibitor at the active site, the inhibitor interacts with the S1, S2 and S4 subsites but not the S3 subsite.

Structurally novel compounds were generated by attaching a piperidine moiety to the dipeptidyl component, to render the compound capable of (a) orienting recognition elements R3 and R4 in a correct vector relationship for optimal interactions (R4/S4 and R3/S3), resulting in a corresponding enhancement in pharmacological activity, and (b) providing a flexible means for the structure-guided parallel optimization of ADMET/PK and physicochemical properties using diversity sites R3 and R4 in inhibitor (I). Further structure-guided design based on GC813 yielded a structurally-novel and IP-robust series of compounds (I), depicted below with their respective subsite interactions indicated:

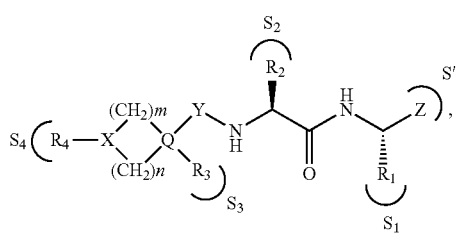

The following specific compounds are generated:

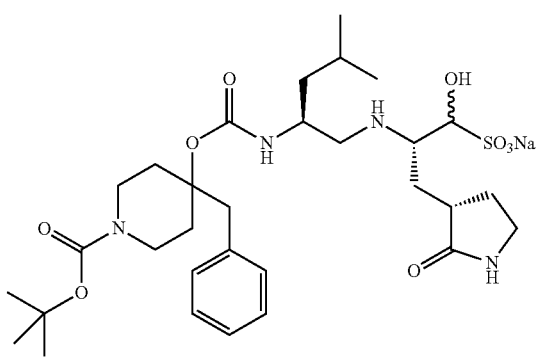

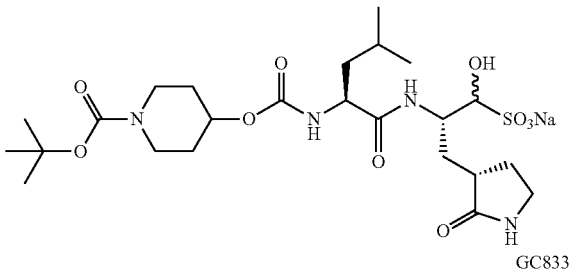

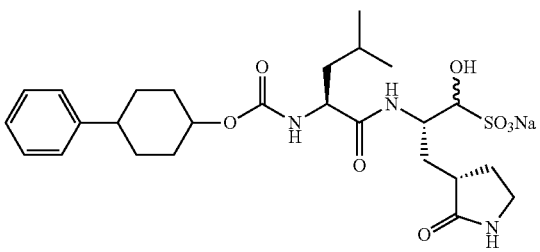

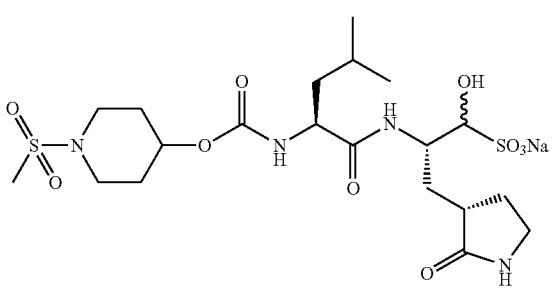

Materials and Methods

Reagents and dry solvents were purchased from various chemical suppliers (Aldrich, Acros Organics, Chem-Impex, TCI America, and Bachem) and were used as obtained. Silica gel (230-450 mesh) used for flash chromatography was purchased from Sorbent Technologies (Atlanta, Ga.). Thin layer chromatography was performed using Analtech silica gel plates. Visualization was accomplished using UV light and/or iodine. NMR spectra were recorded in CDCl$_3$ or DMSO-d$_6$ using a Varian XL-400 spectrometer. Melting points were recorded on a Mel-Temp apparatus and are uncorrected. High resolution mass spectrometry (HRMS) was performed at the University of Kansas Mass Spectrometry lab using an LCT Premier mass spectrometer (Waters, Milford, Mass.) equipped with a time of flight mass analyzer and an electrospray ion source. The purity of the compounds was established using HPLC and was >95%.

Figure 6:
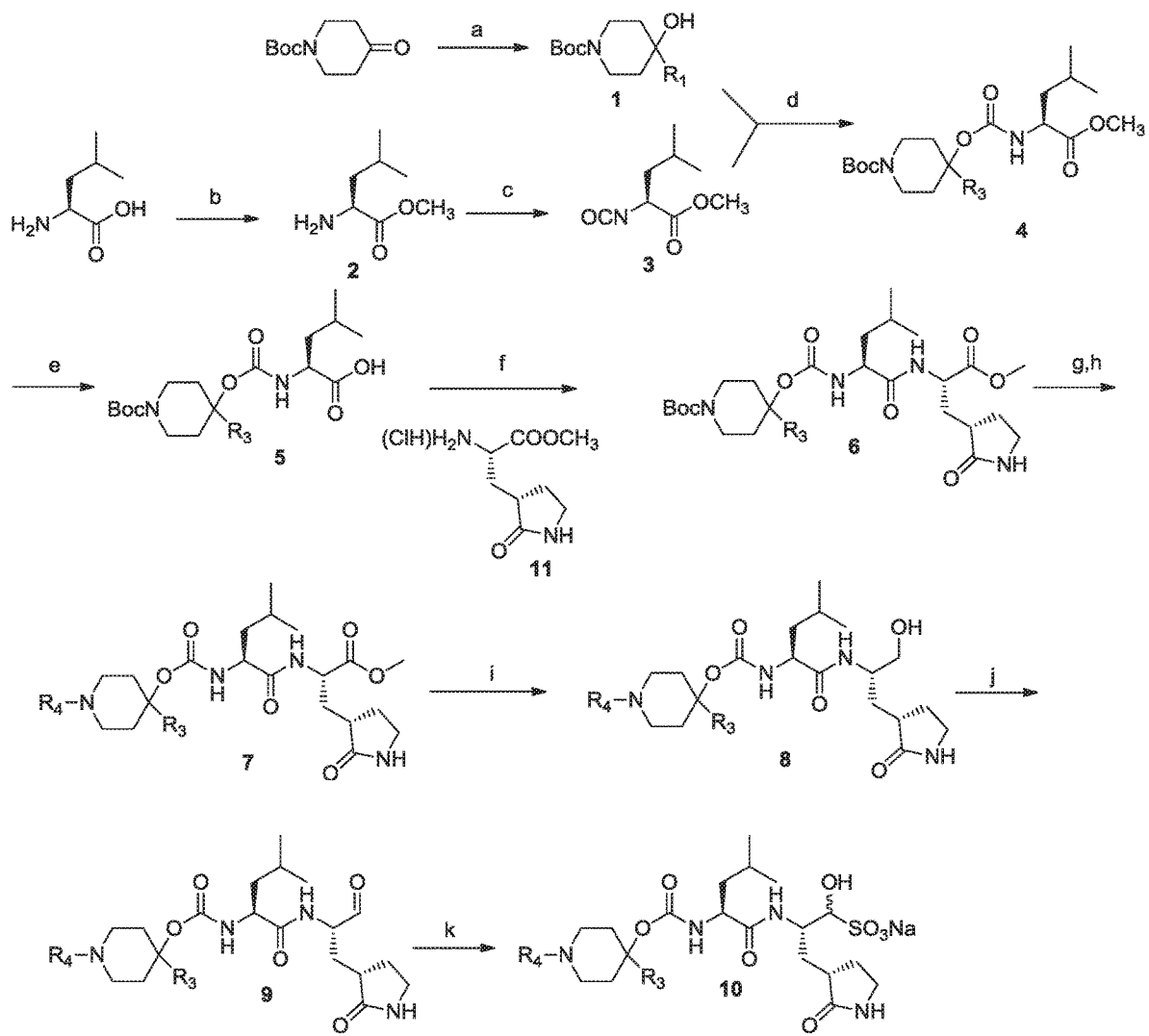
FIG. 6 is a reaction scheme for synthesis of GC861, GC867, and GC868.
Figure 7:
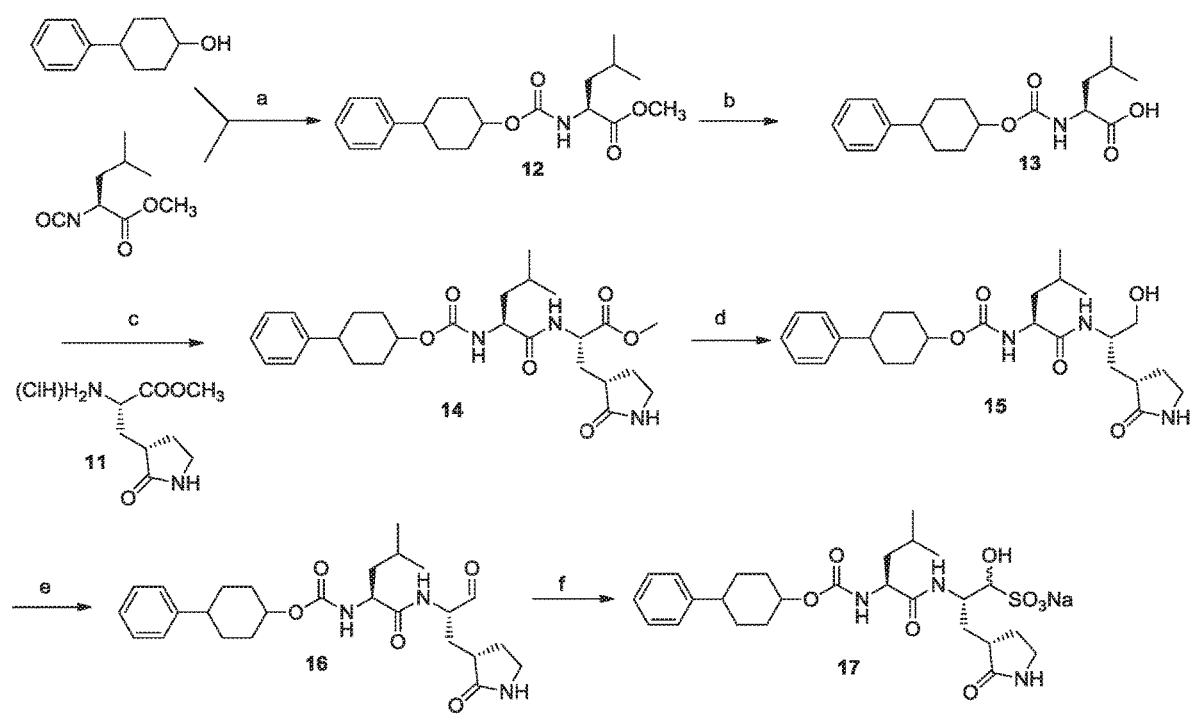
FIG. 7 is a reaction scheme for synthesis of GC833.

The reaction scheme for synthesis of GC861, GC867, and GC868 is illustrated in FIG. 6. The reaction scheme for synthesis of GC833 is illustrated in FIG. 7.

Synthesis of Substituted 1-Boc-4-piperidinols 1

To a solution of 1-Boc-4-piperidinone (10 mmol) in dry THF (15 mL) in ice bath at 0° C. was added appropriate Grignard solution (11 mmol/1.1 eq) drop wise under N$_2$ atmosphere. After the completion of addition of Grignard solution reaction mixture was stirred over 3 h at room temperature under N$_2$ atmosphere while monitoring completion of the reaction by checking TLC. After the completion of reaction, the reaction mixture was diluted with water (25 mL). The solution was acidified to pH ~3 using 5% hydrochloride acid. Then THF was removed on the rotary evaporator and the residue was taken up in ethyl acetate (75 mL) and extracted product in to organic layer from aqueous phase. The organic layer then washed with brine (40 mL) and was separated organic layer from aqueous layer. The EtOAc organic layer was dried over anhydrous sodium sulfate, filtered and concentrated to yield a colorless oily product. Purification by flash chromatography yielded ester 1 as a white solid.

Synthesis of Amino Acid Methyl Esters 2

To a 250 mL RB flask (oven dried and purged with nitrogen) was added absolute methanol (30 mL) and the solution was cooled to 0° C. in an ice bath while kept under a nitrogen atmosphere. Thionyl chloride (8 mL) was added to the cooled methanol with stirring, followed by the addition of the amino acid (100 mmol). The ice bath was replaced by a water bath and the reaction mixture was heated to ~50° C. for 3 h with stirring. Removal of the solvent left a white residue which was washed with diethyl ether (250 mL) and collected by vacuum filtration to yield the amino acid methyl ester hydrochloride 2 as a white solid.

Synthesis of Amino Acid Methyl Ester Isocyanates 3

Amino acid methyl ester hydrochloride (100 mmol) was placed in a dry 500-mL RB flask and then dried overnight on the vacuum pump. The flask was flushed with nitrogen and dry dioxane (200 mL) was added followed by trichloromethyl chloroformate (29.67 g, 150 mmol), and the reaction mixture was refluxed for 10 h. The solvent was removed on the rotary evaporator and the residue was vacuum distilled to yield pure isocyanate 3 as a colorless oil.

Synthesis of Substituted Piperidine-Derived Carbamates 4

A solution of substituted 1-Boc-4-piperidinol (20 mmol) in dry acetonitrile (15 mL) was treated with triethylamine (4.05 g, 40 mmol) followed by the amino acid methyl ester isocyanate (20 mmol). The resulting solution was refluxed for 2 h and then allowed to cool to room temperature. The solution was concentrated and the residue was taken up in ethyl acetate (75 mL). The organic layer was washed with 5% HCl (2×20 mL) and brine (20 mL). The organic layer was dried over anhydrous sodium sulfate, filtered and concentrated, leaving a colorless oil (compound 4). Synthesis of compound 13 for GC833 followed this same general procedure.

Synthesis of Acids 5

A solution of ester 4 (20 mmol) in tetrahydrofuran (30 mL) was treated with 1M LiOH (40 mL). The reaction mixture was stirred for 3 h at room temperature and the disappearance of the ester was monitored by TLC. Most of the solvent was evaporated off and the residue was diluted with water (25 mL). The solution was acidified to pH ~3 using 5% hydrochloride acid (20 mL) and the aqueous layer was extracted with ethyl acetate (3×100 mL). The combined organic layers were dried over anhydrous sodium sulfate, filtered, and concentrated to yield compound 5 as a colorless oil. Synthesis of compound 13 for GC833 followed this same general procedure.

Synthesis of Compounds 6

To a solution of compound 5 (10 mmol) in dry DMF (20 mL) was added EDCI (2.40 g, 12.5 mmol, 1.25 eq), HOBt (1.92 g, 12.5 mmol, 1.25 eq) and the mixture was stirred for 30 minutes at room temperature. In a separate flask, a solution of deprotected glutamine surrogate 12 (2.23 g, 10 mmol) in DMF (15 mL) cooled to 0-5° C. was treated with diisopropylethylamine (DIEA) (9.5 g, 40 mmol, 4 eq), stirred for 30 minutes, and then added to the reaction mixture containing acid. The reaction mixture was stirred for 12 h while monitoring the reaction by TLC. The solvent was removed and the residue was washed between ethyl acetate (100 mL) and 10% citric acid (2×40 mL). The ethyl acetate layer was further washed with saturated aqueous NaHCO$_3$ (40 mL), followed by saturated NaCl (50 mL). The organic layer was dried over anhydrous sodium sulfate, filtered and concentrated to yield a yellow-colored oily product. Purification by flash chromatography yielded ester 6 as a white solid. Synthesis of compound 14 for GC833 followed this same general procedure.

Synthesis of Compounds 7

To a solution of compound 6 (10 mmol) in dry DCM (5 mL) was added 4M HCl in dioxane (8 mL) and the mixture was stirred for an hour at room temperature. The solvent was removed and dried under high vacuum for couple of hours before the product dissolve in dry THF (20 mL). Then appropriate sulfonyl chloride derivative or chloroformate derivative (11 mmol/1.1 eq) was added to stirring solution. Reaction mixture was stirred for 12 h at room temperature. The solvent was removed and the residue was washed between ethyl acetate (50 mL) and 5% HCl (2×20 mL). The ethyl acetate layer was further washed with saturated NaCl (20 mL). The organic layer was dried over anhydrous sodium sulfate, filtered and concentrated to yield a crude product. Purification by flash chromatography yielded ester 7 as a white solid

Synthesis of Alcohols 8

To a solution of ester 7 (5 mmol) in anhydrous THF (30 mL) was added lithium borohydride (2M in THF, 7.5 mL, 15 mmol) dropwise, followed by absolute ethyl alcohol (15 mL), and the reaction mixture was stirred at room temperature overnight. The reaction mixture was then acidified by adding 5% HCl and the pH adjusted to ~2. Removal of the solvent left a residue which was taken up in ethyl acetate (100 mL). The organic layer was washed with brine (25 mL), dried over anhydrous sodium sulfate, filtered, and concentrated to yield compound 8 as a white solid.

Synthesis of Aldehydes 9

Compound 8 (5 mmol) was dissolved in anhydrous dichloromethane (50 mL) under a nitrogen atmosphere and cooled to 0° C. Dess-Martin periodinane reagent (3.18 g, 7.5 mmol, 1.5 eq) was added to the reaction mixture with stirring. The ice bath was removed and the reaction mixture was stirred at room temperature for 3 h (monitoring by TLC indicated complete disappearance of the starting material). A solution of 10% aqueous sodium thiosulfate (20 mL) was added and the solution was stirred for another 15 minutes. The aqueous layer was removed and the organic layer was washed with 10% aqueous sodium thiosulfate (20 mL), followed by saturated aqueous sodium bicarbonate (2×20 mL), water (2×20 mL) and brine (20 mL). The organic layer was dried over anhydrous sodium sulfate, filtered and concentrated. The yellow residue was purified by flash chromatography (silica gel/methylene chloride/ethyl acetate/methanol) to yield a white solid 9. Synthesis of aldehyde 16 for GC833 followed this same general procedure.

Synthesis of Bisulfite Adducts 10

To a solution of aldehyde 9 (5 mmol) in dry ethyl acetate (20 mL) was added absolute ethanol (12 mL) with stirring, followed by a solution of sodium bisulfite (540 mg; 5 mmol) in water (5 mL). The reaction mixture was stirred for 3 h at 50° C. The reaction mixture was allowed to cool to room temperature and then vacuum filtered. The solid was thoroughly washed with absolute ethanol and the filtrate was dried over anhydrous sodium sulfate, filtered, and concentrated to yield yellowish oil. The oily product was treated with ethyl ether (2×50 mL) to form white solid. The white solid was stirred with ethyl ether (30 mL) and ethyl acetate (15 mL) for 5 minutes. Careful removal of the solvent using a pipette left compound 10 as a white solid. Synthesis of bisulfite adduct 17 for GC833 followed this same general procedure.

Figures 8, 9:
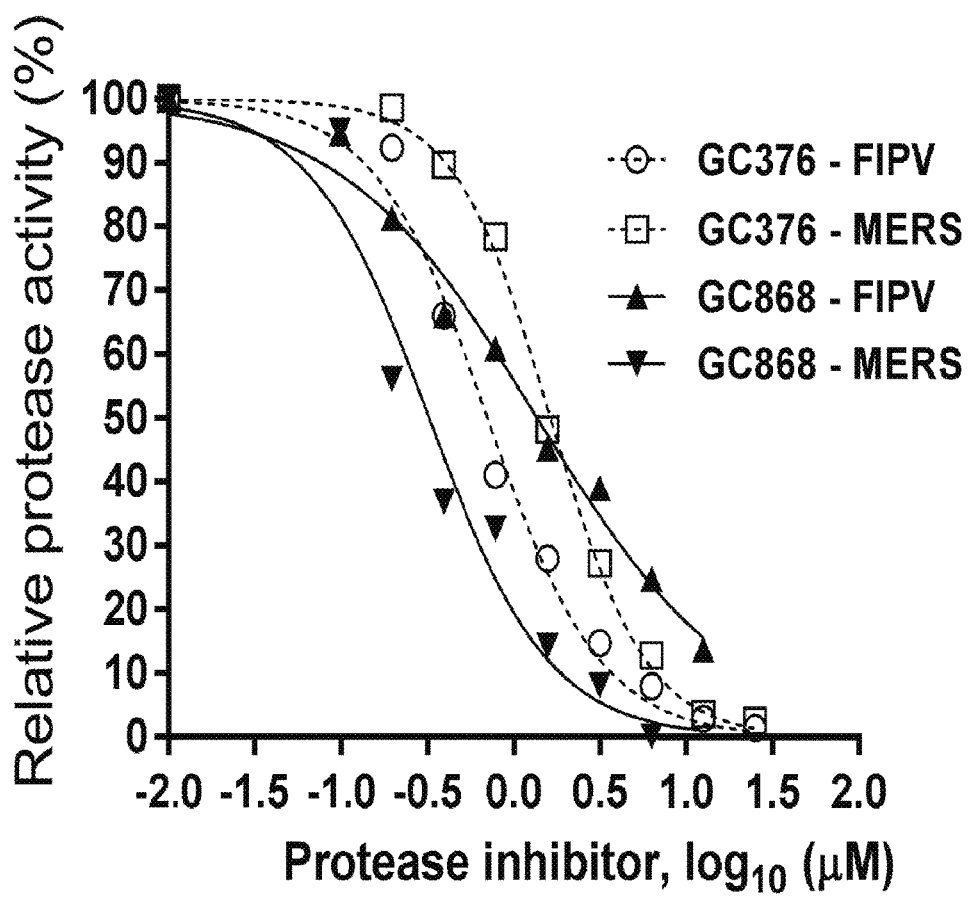
FIG. 8 is a table of the results of enzyme and cell-based assays of effectiveness of dipeptidyl inhibitor compounds and piperidine-based derivatives against MERS-CoV, FIPV, and MHV.
FIG. 9 is a graph of the results of FRET-based assay of effectiveness of dipeptidyl inhibitor compounds and piperidine-based derivative against MERS-CoV and FIPV.

In vitro and cell-based screening with the foregoing derivatives of structure (I) demonstrate the effectiveness of (I), were carried out using the same protocols described above. As shown in FIG. 8 and FIG. 9, these compounds were found to be non-toxic, selective, and highly effective against MERS-CoV, FIPV and murine hepatitis virus (MHV). GC376 was used as a positive control for the tests. Two piperidine-based compounds (including GC868) were tested for selectivity against several human proteases, including α-chymotrypsin, trypsin, thrombin, Factor Xa and plasmin. No or minimal inhibition of these enzymes by the compounds was observed following a 15-minute incubation time at an inhibitor to enzyme ratio of 250. Overall, these compounds displayed broad spectrum activity against the tested coronaviruses with minimal cytotoxicity and excellent selectivity.

Example 3

Figure 10:
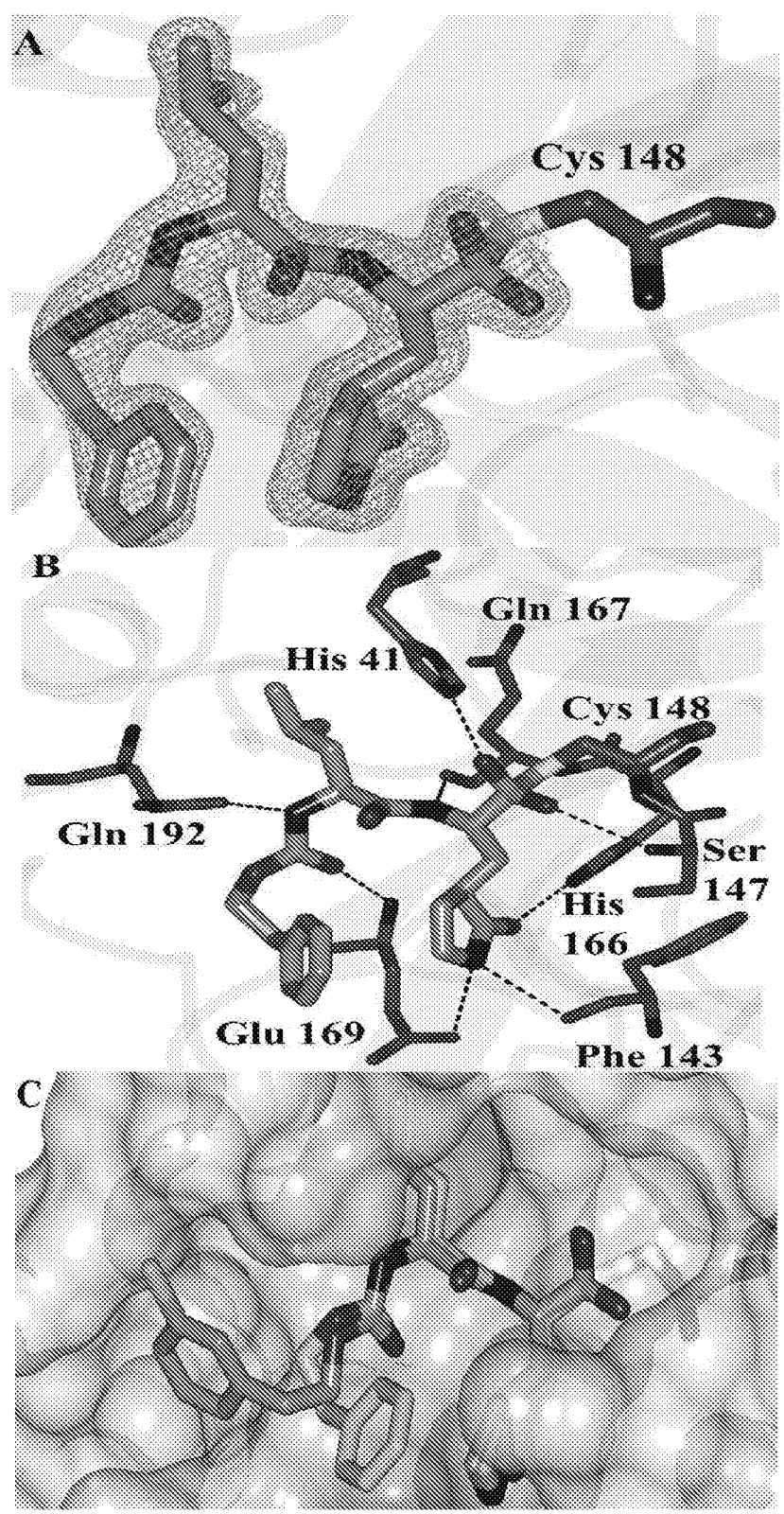
FIG. 10 depicts the crystal structure of GC861. A) Electron density; B) Hydrogen bonding interactions. C) Electrostatic surface with GC861 and GC813 superimposed.

Optimize the Piperidine-Derived Lead Series of MERS-CoV 3CLpro Inhibitors by Iterative Medicinal Chemistry and Structure-Based Drug Design High resolution X-ray crystal structures of several derivatives of (I) bound to MERS-CoV 3CLpro were obtained, including the cocrystal structure of the MERS-CoV 3CLpro:inhibitor GC861 complex. The cocrystal structure of the complex showed that, under the crystallization conditions used, the aldehyde bisulfite adduct reverted to the precursor aldehyde which subsequently formed a tetrahedral adduct with the active site cysteine (Cys148) (FIG. 10A). Inspection of the active site revealed the presence of prominent electron density consistent with inhibitor GC861, however, the N-Boc-piperidinyl moiety was disordered. Inhibitor GC861 is bound to the active site of the enzyme via a network of backbone H-bonds with Gln192, Gln167, and Glu169 (FIG. 10B). Additionally, an H-bond with His41 serves to stabilize the hemi-thioacetal tetrahedral adduct. Also clearly evident are three critical H-bonds involving the P1 Gln surrogate ring oxygen and nitrogen with Glu169, His166 and Phe143. Importantly, the H-bonding interactions are identical to those of inhibitor GC813 (FIG. 2). Furthermore, the structural complementarity of inhibitors GC861 and GC813 is also evident in the electrostatic surface representation of the enzyme with the two inhibitors nestled in the active site (FIG. 10C).

Increased potency and optimal PK can be accomplished using appropriate R3 and R4 substituents, as well as the Z "warhead" component. It should be noted that the proposed piperidine-based design stratagem is a hitherto unrecognized effective way of rendering a dipeptidyl inhibitor equivalent to a tetra-peptidyl inhibitor capable of engaging in optimal binding interactions with all four S1-S4 subsites but which should display diminished PK liabilities because of its reduced peptidyl character.

Design of Z Component.

Warheads (Z) of varying reactivity and physicochemical properties are being investigated, specifically, aldehyde bisulfite adducts where $Z=\!-\!CH(OH)SO_3Na$, $-\!C(OH)(SO_3Na)CONHX$, and bisulfite adducts of α-ketoamides where $Z=\!-\!(C=\!O)CONHX$, where X is alkyl (preferably $C_1$-$C_6$ alkyl), $-\!OR$, or $-\!CHRCOOCH_3$. Dipeptidyl aldehyde bisulfite adducts show promising characteristics of high potency (comparable to that of the precursor aldehydes), no cytotoxicity, and favorable PK characteristics. The PK profiles of the aldehyde bisulfite adducts can also be effectively modulated through the use of ester and carbonate ester precursors ($Z=\!-\!CH(OCOR)SO_3Na$ or $-\!CH(OCOOR)SO_3Na$). We have also demonstrated for the first time that bisulfite adducts of α-ketoamides function as potent inhibitors of viral 3CLpro and we propose herein to evaluate these compounds in greater detail. These α-ketoamides afford greater design flexibility by varying R', which projects toward the S' subsites. Additional work is being carried out on structural variants of α-ketoamides which provide an additional hydrogen bond acceptor site (R'=OR) and are capable of engaging in favorable binding interactions with the S1' subsite of MERS-CoV 3CLpro (R'=CHRCOOCH$_3$). To our knowledge, alkoxy and amino acid-derived structural variants of α-ketoamides have not been described before. In summary, the proposed approach endows inhibitor (I) with superior characteristics, including the ability to exploit favorable binding interactions with the S and S' subsites of the protease and enhances the likelihood of attaining optimal potency, PK, and oral bioavailability profiles, as compared to previous compounds.

Synthesis and Optimization of Inhibitor (I)

A structure-guided approach will continue to be used to subject the identified lead series (I) through iterative cycles of lead optimization to further improve potency, selectivity, and ancillary parameters, such as metabolic stability, solubility, permeability, toxicity (cytotoxicity, CYP enzymes, hERG channel, and P-glycoprotein inhibition), PK characteristics, oral bioavailability, and in vivo efficacy in an animal model. This goal will be achieved by pursuing a lead optimization program that utilizes an integrated and iterative approach involving medicinal chemistry (SAR studies), structure-based drug design, X-ray crystallography, enzyme and cell-based assays, and in vivo animal studies. Thus, compounds will continue to be designed, synthesized, and screened in in vitro and cell-based assays in an iterative fashion with pre-defined benchmarks established for prioritization and advancement. Most importantly, during the lead optimization process, special emphasis will continue to be placed on concurrently optimizing physicochemical properties known to impact favorably PK and oral bioavailability properties by giving due consideration to Lipinski's rule of 5 (MW<500, HBD≤5, HBA≤10, clog P<5) and Veber's guidelines (number of rotatable bonds ≤10, sum of HBD and HBA≤12, PSA≤140 Å). The incorporation of structural features into the lead compounds that are predominantly congruent with these guidelines will likely ensure that drug-likeness is optimized. Our initial focus has been to exploit the high synthetic tractability of (I) and diversity sites R3 and R4, as well as R' in the case of α-ketoamides (the P1 and P2 residues are already optimized and will remain invariant, namely, P1 Leu and P2 Gln surrogate) to develop structure-activity relationships and improve potency while profiling in parallel the ADMET properties of lead compounds using fast pharmacokinetic studies to rapidly ascertain the PK properties of the compounds and conduct full PK studies only with the most promising compounds. In short, antiviral activity and ADMET/PK will be optimized in parallel. The high synthetic tractability of (I), the methodologies employed, and the extensive synthetic and medicinal chemistry expertise available to the project, are expected to yield the desired analogs expeditiously. As mentioned earlier, a P1 Gln surrogate will be used for synthetic tractability and a P2 Leu (the P2 residue strongly preferred by MERS 3CLpro) for optimal hydrophobic interactions with the S2 subsite. Because the P1 and P2 residues remain invariant, the optimization plan entails the sequential optimization of R4, then X (in α-ketoamides) and, finally, R3.

Structure-Guided Design of R4 of Inhibitor GC868.

GC868

$R_4 = $ —COOC(CH$_3$)$_3$

Figure 11:
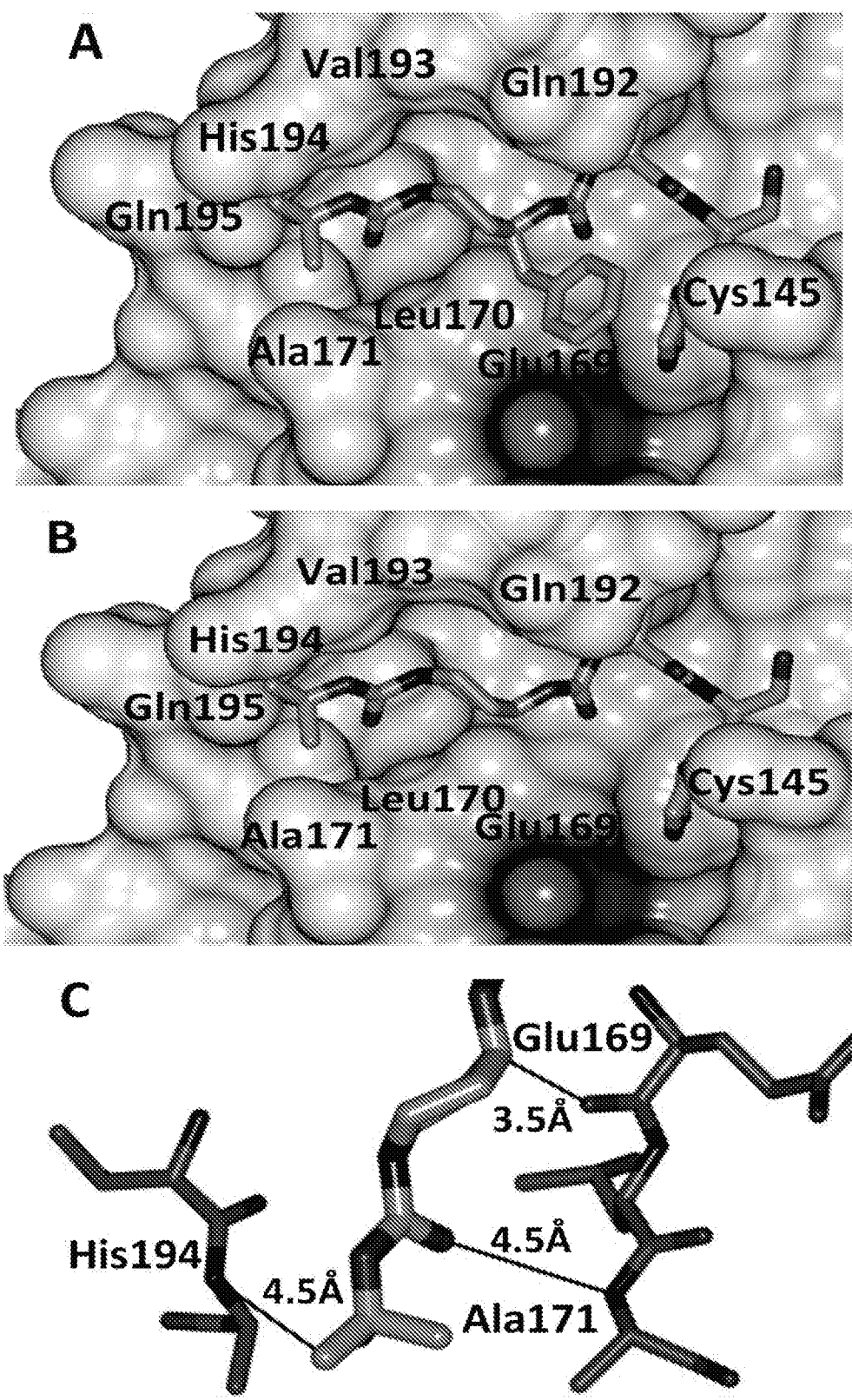
FIG. 11 depicts an electrostatic surface representation of A) GC861 and B) GC868. The N-Boc-piperidinyl ring was modeled in an idealized position for each structure. C) Distances between the piperidine and BOC groups in the idealized structure of GC868.

The N-Boc-piperidinyl in the structure of GC861 is disordered, however, since the position of the benzyl group could be discerned from the electron density maps, the N-Boc-piperidinyl moiety was placed in an idealized position and is positioned in a relatively hydrophobic cleft of the S4 subsite surrounded by Ala171, Leu170, Val193, His194 and Gln195 (FIG. 1A). The lack of hydrogen bond contacts for this segment of the inhibitor most likely results in the observed disorder. Likewise, the N-Boc-piperidinyl moiety in the idealized structure of GC868, which does not possess the benzyl group, is expected to adopt a similar binding mode (FIG. 11B). Inspection of FIG. 11B revealed opportunities for additional binding interactions with a more efficient use of chemical structure. By way of illustration, one such opportunity was recognized by observing that the N-Boc-carbonyl and methyl groups are positioned 4.5 Å from the backbone nitrogen atoms of Ala171 and His194 (FIG. 11C). Thus, we envisage that the replacement of the N-Boc group in inhibitor GC868 with an appropriate functional group (computational and docking studies suggest R4=RSO$_2$ and RO(C=O) are optimal) could serve as a locus for the formation of one or more H-bonds with Ala171 and His194, as well as engage in hydrophobic interactions, thereby increasing binding affinity by stabilizing the N-Boc-piperidine moiety and "locking" the inhibitor in the S4 subsite.

Figure 12:
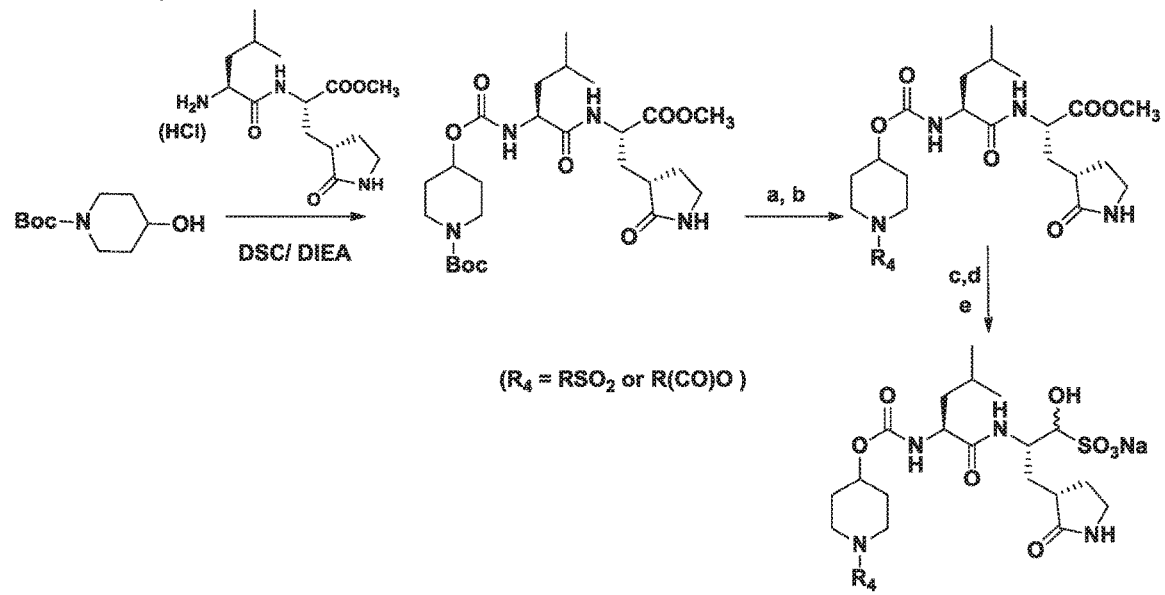
FIG. 12 illustrates a reaction scheme of design of R4 substituent of GC868.

Because the precise position of the N-substituted piperidine moiety is not currently known, the aforementioned hypothesis will be evaluated via the construction of two focused libraries (ten members each) with R$_4$=RSO$_2$ and RO(C=O) using commercially-available sulfonyl chlorides and alkyl chloroformates pre-filtered in terms of computational- and modeling-based active site fit, ability to engage in H-bonding and hydrophobic interactions, and high stability. Thus, coupling of N-Boc-4-piperidinol with readily-available dipeptide (A) using N,N'-disuccinimidyl carbonate (DSC) followed by removal of the Boc group yields a piperidine-based dipeptide ester which is subsequently coupled individually to a ten-member set of sulfonyl chlorides and a ten-member set of alkyl chloroformates. Further elaboration of each member of the generated libraries is anticipated to yield the aldehyde bisulfite adducts as shown in FIG. 12.

Screening of the bisulfite adducts will likely reveal the identity of the optimal R4 group in GC868. Such "cap" modifications have been highly successful in improving the pharmacological activity, selectivity and PK profiles of HCV NS3/4A protease inhibitors.

Structure-Guided Design of R' of Inhibitor GC868.

Once R$_4$ is optimized and, since the P1 and P2 residues are already fixed, the design of R' will be expeditiously accomplished using the Passerini reaction.

Figure 13:
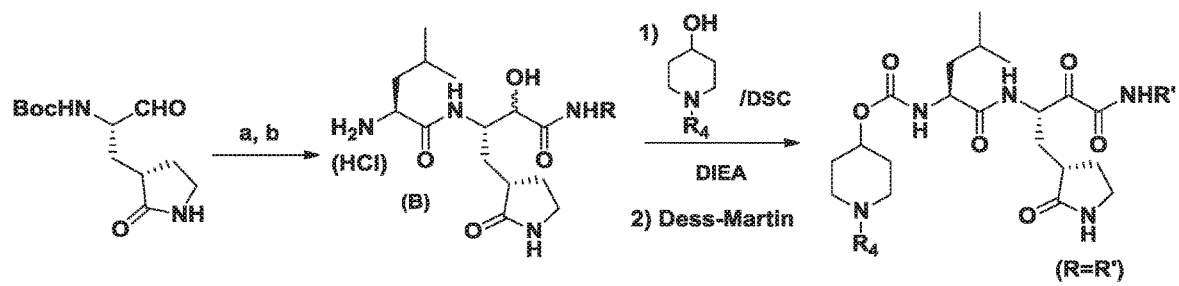
FIG. 13 illustrates a reaction scheme of the synthesis of alpha-ketoamides using Passerini reaction and design of the R' group.

Thus, a structurally-diverse set of alkyl, alkoxy and amino acid-derived isonitriles will be used to generate a focused library of α-hydroxyketoamides (B) as shown in FIG. 13.

The desired alkyl, alkoxy and amino acid-derived isonitriles can be readily synthesized from the precursor N-formamides. The α-hydroxyketoamides will be subsequently coupled individually to the appropriate 4-piperidinol bearing previously-optimized R4 (vide supra) using N,N'-disuccinimidyl carbonate (DSC) followed by Dess-Martin oxidation to yield a series of structurally-diverse α-ketoamides which will be evaluated for their activity against MERS-CoV 3CLpro in vitro and cell-based assays. The generated α-ketoamides will be prioritized and the top 2-3 α-ketoamides will be used to evaluate enzyme selectivity, conduct preliminary PK studies, and obtain high-resolution cocrystal structures with MERS-CoV 3CLpro. Our primary objective at this stage is to identify optimal R4 and Z moieties in inhibitor (I) that result in improved potency and selectivity and, most importantly, display satisfactory PK characteristics.

Structure-Guided Design of R3.

Figure 14:
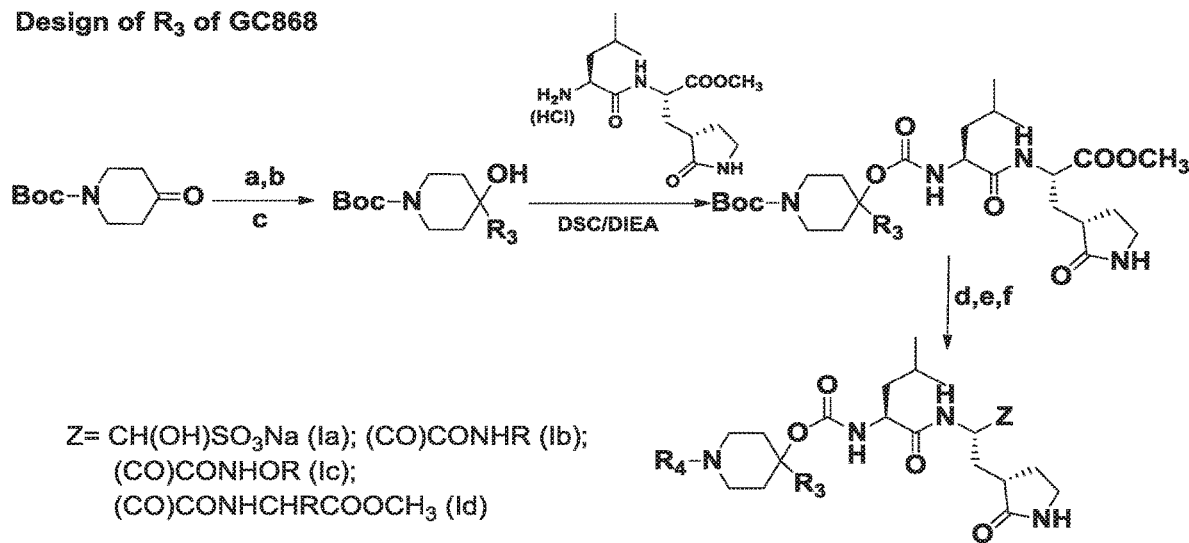
FIG. 14 illustrates a reaction scheme of design of $R_3$ substituent of GC868.

Further design of pharmacological activity, selectivity and ancillary PK parameters is envisioned to involve optimization of R3 as shown in FIG. 14, as a means of ultimately identifying 2-3 lead compounds suitable for conducting further pre-clinical studies.

Figure 15:
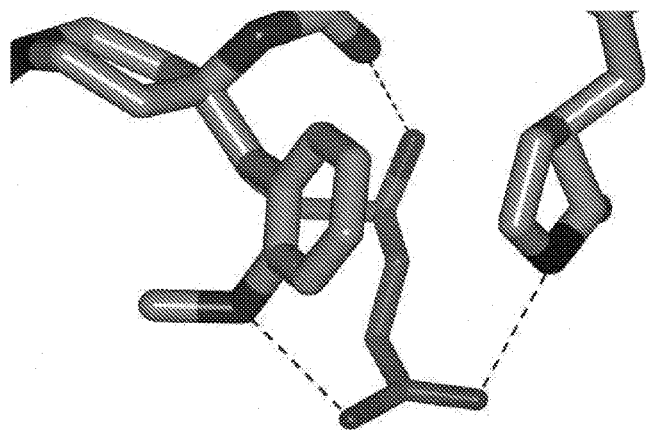
FIG. 15 depicts a representation of benzyl ring substitution for GC861. Addition of a methoxy group at the ortho position would place the oxygen atom of the substituent approximately 3 Å from Glu 169 and permit formation of a new hydrogen bond.

Inspection of the crystal of the MERS-CoV:inhibitor GC861 suggests that the presence of a H-bond acceptor, such as a —OCH$_3$ group, at the ortho position would allow the formation of a H-bond with Glu169 (FIG. 15). The main objective is to optimize lead series (I) and identify a preclinical candidate, as well as 1-2 back up compounds, with optimal pharmacological activity and PK profiles that are well-suited to conducting further preclinical studies. In summary, the long term goal of these endeavors is the identification of a drug candidate for the treatment of MERS-CoV infection (Target milestones: EC50<0.05 μM, CC50>100 μM).

Example 5

Macrocyclic Inhibitors

In this Example, new classes of compounds is described that are macrocyclic-derivatives of Structure I, described above.

Figure 16:
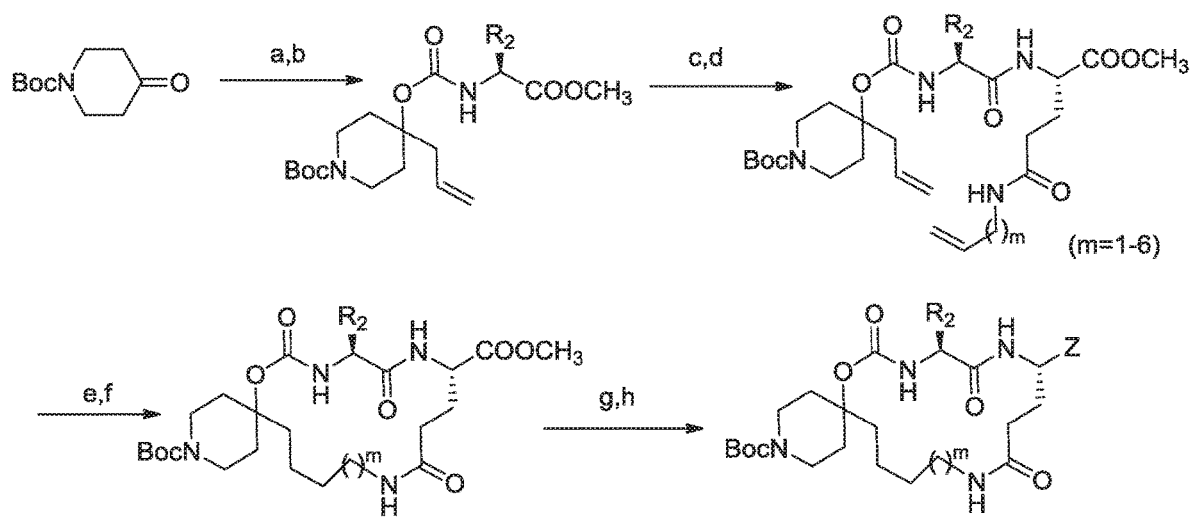
FIG. 16 illustrates a reaction scheme of the general synthesis of piperidine-based derivatives of structure II.

Piperidine-based spiro macrocycles are particularly promising and novel, as illustrated in the exemplary reaction scheme depicted in FIG. 16.

The invention claimed is:

1. An antiviral compound comprising formula I:

or a pharmaceutically-acceptable salt thereof, where:
X is CH or N;
Z is —CH(OH)SO$_3$Na or —(C═O)(C═O)NHR, where each R is selected from the group consisting of alkyls, haloalkyls, phenyls, and arylalkyls;
R$_1$ is Gln or a Gln surrogate side chain;
R$_2$ is a branched or unbranched alkyl;
R$_3$ is selected from the group consisting of —H and arylalkyls; and
R$_4$ is selected from the group consisting of —SO$_2$R and —COOR, where each R is selected from the group consisting of alkyls and phenyls.

2. The compound of claim 1, wherein said compound inhibits viral replication of one or more viruses selected from the group consisting of Middle East Respiratory Syndrome Coronavirus (MERS-CoV), Feline infections Peritonitis virus (FIPV) and Murine hepatitis virus (MHV).

3. The compound of claim 1, wherein said compound is selected from the group consisting of:

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Synthetic FRET substrate

<400> SEQUENCE: 1

Lys Thr Ser Ala Val Leu Gln Ser Gly Phe Arg Lys Met Glu
1               5                   10

GC867

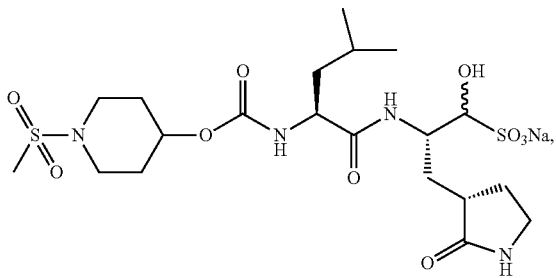

GC868

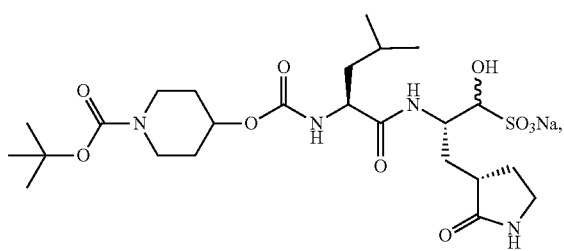

GC833

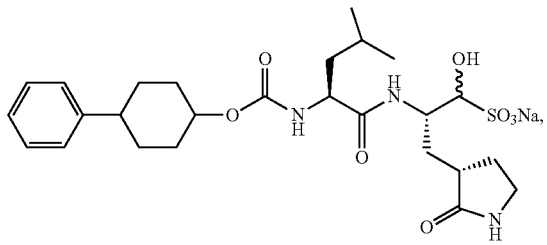

and pharmaceutically-acceptable salts thereof.

4. The compound of claim 1, wherein said Gln surrogate side chain is —CH$_2$W, where W is 1-pyrrolidinyl, 3-pyrrolidinyl, —CH$_2$CON(CH$_3$)$_2$, or —CH$_2$NHCOR$_5$, where R$_5$ is alkyl, phenyl or arylalkyl.

5. A antiviral composition comprising a first antiviral compound according to claim 1 dispersed in a pharmaceutically-acceptable carrier.

6. The composition of claim 5, further comprising a second antiviral compound, both of said compounds being dispersed in said pharmaceutically-acceptable carrier.

7. The composition of claim 6, wherein said second compound is an antiviral compound according to claim 1, said first compound being different from said second compound.

* * * * *